United States Patent
Duan et al.

(10) Patent No.: US 10,829,437 B2
(45) Date of Patent: Nov. 10, 2020

(54) NITROBENZYL DERIVATIVES OF ANTI-CANCER AGENTS

(71) Applicants: OBI PHARMA, INC., Taipei (TW); ASCENTA PHARMACEUTICALS, LTD., Guangdong (CN)

(72) Inventors: Jian-Xin Duan, South San Francisco, CA (US); Yeyu Cao, South San Francisco, CA (US); Xiaohong Cai, South San Francisco, CA (US); Hailong Jiao, South San Francisco, CA (US); Jing Yuan Ma, South San Francisco, CA (US); Mark Matteucci, South San Francisco, CA (US)

(73) Assignee: OBI PHARMA, INC., Taipei (TW)

( * ) Notice: Subject to any disclaimer, the term of this patent is extended or adjusted under 35 U.S.C. 154(b) by 0 days.

(21) Appl. No.: 15/563,481

(22) PCT Filed: Apr. 1, 2016

(86) PCT No.: PCT/US2016/025665
§ 371 (c)(1),
(2) Date: Sep. 29, 2017

(87) PCT Pub. No.: WO2016/161342
PCT Pub. Date: Oct. 6, 2016

(65) Prior Publication Data
US 2018/0086693 A1    Mar. 29, 2018

Related U.S. Application Data

(60) Provisional application No. 62/142,352, filed on Apr. 2, 2015.

(51) Int. Cl.
| | | |
|---|---|---|
| C07C 217/58 | (2006.01) | |
| C07C 213/02 | (2006.01) | |
| C07D 405/12 | (2006.01) | |
| C07D 491/22 | (2006.01) | |
| C07H 19/06 | (2006.01) | |
| C07F 9/6558 | (2006.01) | |
| A61K 47/64 | (2017.01) | |
| C07D 403/06 | (2006.01) | |
| A61K 47/55 | (2017.01) | |
| A61P 35/00 | (2006.01) | |
| C07D 239/94 | (2006.01) | |
| C07D 487/04 | (2006.01) | |
| C07D 471/04 | (2006.01) | |
| A61K 47/54 | (2017.01) | |

(52) U.S. Cl.
CPC ............ *C07C 217/58* (2013.01); *A61K 47/55* (2017.08); *A61K 47/64* (2017.08); *A61P 35/00* (2018.01); *C07C 213/02* (2013.01); *C07D 239/94* (2013.01); *C07D 403/06* (2013.01); *C07D 405/12* (2013.01); *C07D 471/04* (2013.01); *C07D 487/04* (2013.01); *C07D 491/22* (2013.01); *C07F 9/65586* (2013.01); *C07H 19/06* (2013.01); *A61K 47/54* (2017.08)

(58) Field of Classification Search
CPC ... C07C 217/58; C07C 213/02; C07D 491/22; C07D 405/12; C07H 19/06
USPC .......................................................... 514/49
See application file for complete search history.

(56) References Cited

U.S. PATENT DOCUMENTS

| | | |
|---|---|---|
| 5,472,956 A | 12/1995 | Borch et al. |
| 6,482,953 B1 | 11/2002 | Kim et al. |
| 8,507,464 B2 | 8/2013 | Matteucci et al. |
| 2004/0214798 A1 | 10/2004 | Hu |
| 2008/0269268 A1 | 10/2008 | Schirok et al. |
| 2010/0256139 A1 | 10/2010 | Rockway et al. |
| 2011/0251159 A1 | 10/2011 | Matteucci et al. |
| 2014/0010805 A1 | 1/2014 | Hart et al. |
| 2014/0170240 A1 | 6/2014 | Matteucci et al. |
| 2018/0044360 A1* | 2/2018 | Duan .................... C07F 9/2466 |

FOREIGN PATENT DOCUMENTS

| | | |
|---|---|---|
| CN | 102924507 A | 2/2013 |
| JP | 2018-513876 A | 5/2018 |
| WO | WO-2004/087075 | 10/2004 |
| WO | WO-2006/057946 A2 | 6/2006 |

(Continued)

OTHER PUBLICATIONS

Hay et al. Substituent effects on the kinetics of reductively-initiated fragmentation of nitrobenzyl carbamates designed as triggers for bioreductive prodrugs. J. Chem. Soc., Perkin Trans. 1, 1999, 2759-2770. (Year: 1999).*

(Continued)

*Primary Examiner* — Yih-Horng Shiao
(74) *Attorney, Agent, or Firm* — Foley & Lardner LLP

(57) ABSTRACT

Provided herein are compounds of formula I, wherein the variables are defined herein, processes of making them, and methods of treating cancer comprising administering such compounds.

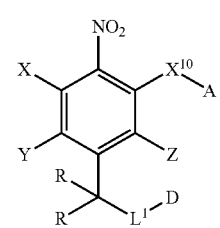

16 Claims, No Drawings

(56) References Cited

FOREIGN PATENT DOCUMENTS

| WO | WO-2007/002931 A2 | 1/2007 |
|---|---|---|
| WO | WO-2007/098089 A2 | 8/2007 |
| WO | WO-2008/083101 A1 | 7/2008 |
| WO | WO-2008/151253 A1 | 12/2008 |
| WO | WO-2009/018163 A1 | 2/2009 |
| WO | WO-2010/044686 A1 | 4/2010 |
| WO | WO-2010/048330 A1 | 4/2010 |
| WO | WO-2011/066416 A1 | 6/2011 |
| WO | WO-2014/131023 A1 | 8/2014 |
| WO | WO-2015/051921 A1 | 4/2015 |
| WO | WO-2016/145092 A1 | 9/2016 |
| WO | WO-2016/161342 A2 | 10/2016 |
| WO | WO-2016/210175 A1 | 12/2016 |
| WO | WO-2017/087428 A1 | 5/2017 |

OTHER PUBLICATIONS

Rastelli et al. Discovery of New Inhibitors of Aldose Reductase from Molecular Docking and Database Screening. Bioorganic & Medicinal Chemistry 10 (2002) 1437-1450. (Year: 2002).*
Costantino et al. Nitrophenyl Derivatives as Aldose Reductase Inhibitors. Bioorganic & Medicinal Chemistry 10 (2002) 3923-3931. Year: 2002).*
Juneja et al. Mutagenicity of nitrobenzyl derivatives: potential bioreductive anticancer agents. Mutation Research 348 (1995) 137-145. (Year: 1995).*
Juneja et al. Mutagenicity of sulfoscanate: a comparative study. Mutation Research 518 (2002) 155-161. (Year: 2002).*
Guise, C.P. et al. (2014) "Bioreductive prodrugs as cancer therapeutics: targeting tumor hypoxia," Chinese Journal of Cancer 33(2):80-86.
International Search Report and Written Opinion (ISA/US) for International Application No. PCT/US2016/025665, dated Sep. 8, 2016.
Jain, M. et al. (2004) "Sulfonyl-containing aldophosphamide analogues as novel anticancer prodrugs targeted against cyclophosphamide-resistant tumor cell lines," Journal of Medicinal Chemistry 47(15):3843-3852.
Mulcahy, R.T. et al. (1994) "Nitrobenzyl phosphorodiamidates as potential hypoxia-selective alkylating agents", Journal of Medicinal Chemistry 37:1610-1615.
Duan, J-X. et al. (2008) "Potent and Highly Selective Hypoxia-Activated Achiral Phosphoramidate Mustards as Anticancer Drugs," J. Med Chem 51:2412-2420.
Golub, T.R. et al. (1999) "Molecular Classification of Cancer: Class Discovery and Class Prediction by Gene Expression Monitoring," Science 286:531-537.
NIH National Cancer Institute (2015) "Targeted Cancer Therapies Fact Sheet," see http://www.cancer.gov/about-cancer/treatment/types/targeted-therapies/targeted-therapies-fact-sheet, accessed Dec. 8, 2015.
Non-Final Office Action in U.S. Appl. No. 15/326,990, dated Apr. 30, 2018.
Non-Final Office Action in U.S. Appl. No. 15/557,053, dated Jun. 22, 2018.
Notice of Allowance in U.S. Appl. No. 15/326,990, dated Jul. 5, 2018.
Chen, Y. et al., "Design of anticancer prodrugs for reductive activation", Medicinal Research Reviews, vol. 29, No. 1, 2009, pp. 29-64.
Communication pursuant to Rules 70(2) and 70a(2) EPC issued in EP 16815334.4 dated Jan. 8, 2019, 1 page.
Extended European search report issued in 16762438.6 dated Jul. 3, 2018, 10 pages.
Extended European Search Report issued in 16774352.5 dated Nov. 6, 2018, 11 pages.
Extended European Search Report issued in 16815334.4 dated Dec. 21, 2018, 7 pages.
Hu et al., "Synthesis and structure-activity relationships of nitrobenzyl phosphoramide mustards as nitroreductase-activated prodrugs", Bioorganic & Medicinal Chemistry Letters 21 (2011) 3986-3991.
International Preliminary Report on Patentability issued in PCT/US2016/039092 dated Jan. 4, 2018, 9 pages.
K. Misiura et al., "Stereospecific synthesis of chiral metabolites of Ifosfamide and their determination in the Urine", Journal of Medicinal Chemistry., vol. 26, 1983, pp. 674-679, XP002786859, USAMERICAN Chemical Society. Washington. ISSN: 0022-2623.
Li, Z. et al., "Nitrobenzocyclophosphamides as Potential Prodrugs for Bioreductive Activation: Synthesis, Stability, Enzymatic Reduction, and Antiproliferative Activity in Cell Culture", Bioorganic & Medicinal Chemistry, vol. 11, No. 19, 2003, pp. 4171-4178.
Non-Final Office Action on U.S. Appl. No. 15/736,285 dated Sep. 27, 2018 (9 pgs).
Non-Final Office Action on U.S. Appl. No. 15/752,854 dated Nov. 20, 2018 (11 pgs).
Notice of Allowance on U.S. Appl. No. 15/326,990 dated Oct. 15, 2018 (5 pgs).
Notice of Allowance on U.S. Appl. No. 15/557,053 dated Dec. 28, 2018 (9 pgs).
Notice of Allowance on U.S. Appl. No. 15/736,285 dated Jan. 24, 2019 (12 pgs).
Nakagawara, A., Trk receptor tyrosine kinases: a bride between cancer and neural development, Cancer Letters, 2001, 169:107-114.
Non-Final Office Action issued in U.S. Appl. No. 16/368,753 dated Oct. 7, 2019.

* cited by examiner

NITROBENZYL DERIVATIVES OF ANTI-CANCER AGENTS

CROSS-REFERENCE TO RELATED APPLICATIONS

This application is a national stage application under 35 U.S.C. § 371 of International Application No. PCT/US2016/025665, filed Apr. 1, 2016, which in turn claims priority under 35 U.S.C. § 119(e) to U.S. Provisional Patent Application No. 62/142,352, filed Apr. 2, 2015, the content of each of which is hereby incorporated by reference in its entirety.

FIELD OF INVENTION

The present invention provides compounds suitable as therapeutic agents and intermediates thereto, pharmaceutical compositions of such compounds and methods of treating cancer in cancer patients, and so relates to the fields of biology, chemistry, and medicine.

BACKGROUND

Cancer is one of the major causes of human morbidity and mortality. Cancer treatment is challenging because it is difficult to kill cancer cells without damaging or killing normal cells. Damaging or killing normal cells during cancer treatment is a cause of adverse side effects in patients and can limit the amount of anti-cancer drug administered to a cancer patient.

Aldo-keto reductase family 1 member C3 is an enzyme that in humans is encoded by the AKR1C3 gene. This gene encodes a member of the aldo/keto reductase superfamily, which consists of more than 40 known enzymes and proteins. These enzymes catalyze the conversion of aldehydes and ketones to their corresponding alcohols by utilizing NADH and/or NADPH as cofactors.

Many cancer cells overexpress AKR1C3 reductase relative to normal cells (See, Cancer Res 2010; 70:1573-1584, Cancer Res 2010; 66: 2815-2825). PR 104:

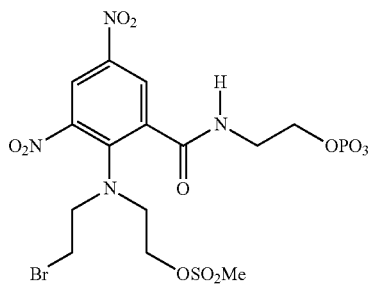

PR 104P has been shown to be a weak substrate for AKR1C3 and was tested in the clinical trials as the water soluble phosphate prodrug PR 104P. This compound is not a selective AKR1C3 activated prodrug as it can also be activated under hypoxic conditions. PR104 was ineffective in clinical trials.

There remains a need for compounds suitable for treating cancer patients, including for selective AKR1C3 reductase activated prodrugs for treating cancer patients. The present invention meets this need.

SUMMARY

In one aspect, provided herein are compounds of formula I:

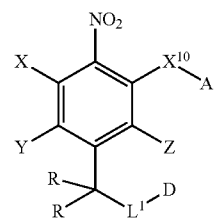

pharmaceutically acceptable salts, and solvates of each thereof, wherein $X^{10}$ is O, S, SO, or $SO_2$;

A is $C_6$-$C_{10}$ aryl, 5-15 membered heteroaryl, or —N=$CR^1R^2$;

each $R^1$ and $R^2$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each X, Y, and Z independently is hydrogen, CN, halo, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$; or —$NR^{13}COR^{14}$;

each R independently is hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$; or —$NR^{13}COR^{14}$;

each $R^{13}$ and $R^{14}$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, or ether;

wherein $L^1$ and D are defined as follows:

$L^1$ is selected from:

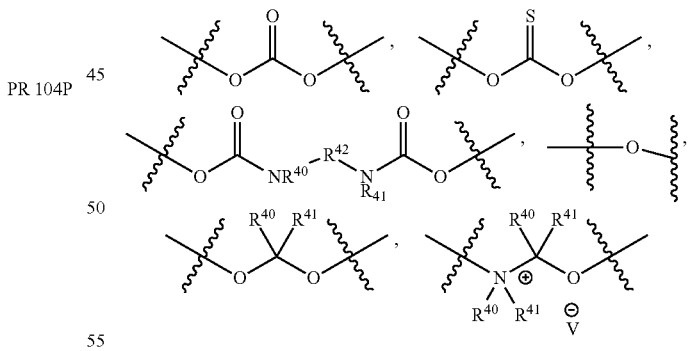

$R^{40}$ and $R^{41}$ are independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, or 5-15 membered heteroaryl $R^{42}$ is $C_2$-$C_3$ alkylene or heteroalkylene optionally substituted with 1-3 $C_1$-$C_6$ alkyl groups, V(−) is any anion, preferably, a pharmaceutically acceptable anion, D is a moiety such that D-OH is an anti cancer drug wherein OH is an aliphatic or a phenolic hydroxy group or is an OH moiety attached to a phosphorous atom as provided herein; or $L^1$ is:

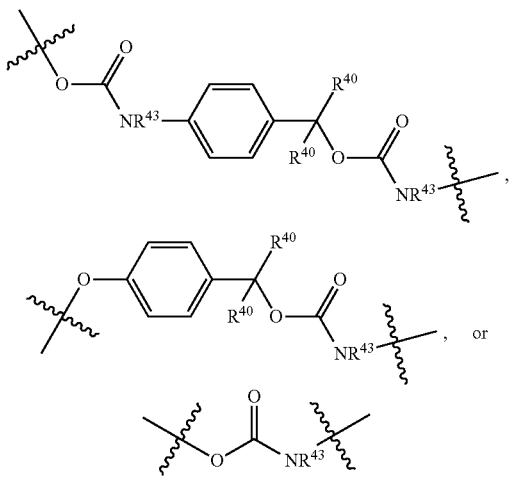

$R^{40}$ is defined as above, $R^{43}$ is hydrogen or together with D forms a heterocycle ring, and the phenylene moiety is optionally substituted, and D is a moiety such that $D-NR^{43}H$ is an anti cancer drug; or $L^1$ is a bond, $-O-CR^{40}R^{41}{}_2-$, $-O-C(R^{40}R^{41})-NR^{40}R^{41}(+)-C(R^{40}R^{41})-$, or

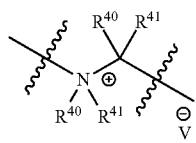

wherein $R^{40}$ and $R^{41}$ are defined as above, and D is an anticancer drug containing a tertiary or a secondary nitrogen atom, wherein the tertiary or the secondary nitrogen atom is bonded to $L^1$, wherein the alkyl, alkenyl, alkynyl, cycloalkyl, aryl, heterocycle, heteroaryl, and ether groups are optionally substituted.

In another embodiment, provided herein is a compound of formula I-A

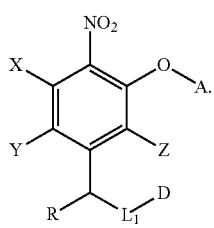

In another embodiment, $X^{10}$ is S.

Illustrative and non-limiting examples of D, and how D is bonded to $L^1$ is provided herein. Based on this information, other D useful moieties and their bonding to $L^1$ in accordance with this invention will be apparent to a skilled artisan.

As used herein, D excludes a phosphoramidate alkylator such as $-P(Z^1)(NR^{30}CH_2CH_2X^1)_2$, $-P(Z^1)(NR^{30}{}_2)(N(CH_2CH_2X^1)_2)$, $-P(Z^1)(N(CH_2CH_2))_2$, or $-P(Z^1)(N(CH_2CH_2X^1)_2)_2$, wherein each $R^{30}$ independently is hydrogen or $C_1$-$C_6$ alkyl or 2 $R^{30}$s together with the nitrogen atom they are bound to form 5-7 membered heterocyclyl group, $Z^1$ is O or S, and $X^1$ is Cl, Br, or OMs or another leaving group.

In some embodiment, the compounds provided herein have an anti-cancer cellular cytotoxicity or anti-proliferation effect that is at least half, at least 20%, at least 10%, at least 5%, at least 1%, or at least 0.1% of the corresponding anti cancer agent: DOH, $DNH_2$, and the likes, as utilized herein. Methods of determining the cytotoxicity or the anti-proliferation effect of compounds are well known to the skilled artisan and also described herein. In some embodiment, those hydroxy and amino (including secondary and tertiary amino groups) groups in an anti cancer agents are derivatized as provided herein such that upon derivatization and forming the compounds of this invention, the cytotoxity or the antiproliferation effect of the derivative (i.e., the compound provided herein) is at least half, at least 20%, at least 10%, at least 5%, at least 1%, or at least 0.1% of the corresponding anti cancer agent utilized. Skilled artisan are aware of which hydroxy and/or amino groups (including secondary and tertiary amino groups) of an anti cancer agent are responsible for at least some or a substantial part of the anti cancer activity of that agent. For example, and without limitation, masking the amino group in an anthracycline as provided herein, is contemplated to reduce the cytotoxicity of the anthracycline.

The compounds provided herein include individual diastereomers and other geometric isomers, and enantiomers, and mixtures of enantiomers, diastereomers, and geometric isomers other than diastereomers.

In another aspect, provided herein is a pharmaceutical composition comprising a compound provided herein and at least one pharmaceutically acceptable excipient. In another aspect, provided herein is a unit dose of the pharmaceutical composition provided herein.

In another aspect, provided herein is a method for treating cancer in a patient, comprising administering to the patient a therapeutically effective amount of a compound or a pharmaceutically acceptable composition as provided herein. In one embodiment, the cancer is one wherein AKR1C3 reductase levels are high or are higher than usual in such a cancer. In one embodiment, the cancer is liver cancer. In one embodiment, the cancer is non small cell lung cancer or melanoma. In a further aspect, the method comprises determining the AKR1C3 reductase level of the cancer by methods using an AKR1C3 antibody, and administering a therapeutically effective amount of a compound or a pharmaceutically acceptable composition provided herein to said patient if said level is equal to or greater than a predetermined value. In one aspect, the method comprises prior to administration, determining a intratumoral AKR1C3 reductase level in a sample isolated from the patient and selecting the patient for the therapy if the level is equal to or greater than a predetermined level. In some embodiments, a therapeutically effective amount of a cancer treatment other than a treatment comprising administration of a compound or a pharmaceutically acceptable composition provided herein is administered if the level does not exceed or is less than said predetermined value. Methods of determining the therapeutically effective amount, appropriate mode of administration of the compounds and compositions provided herein will be apparent to the skilled artisan upon reading this disclosure and based on other methods known to them.

AKR1C3 levels are measured following routine methods well known to the skilled artisan.

DETAILED DESCRIPTION

Definitions

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"$C_x$-$C_y$" or "$C_{x-y}$" before a group refers to a range of the number of carbon atoms that are present in that group. For example, $C_1$-$C_6$ alkyl refers to an alkyl group having at least 1 and up to 6 carbon atoms.

"Alkoxy" refers to —O-Alkyl.

"Amino" refers to $NR^pR^q$ wherein $R^p$ and $R^q$ independently are hydrogen or $C_1$-$C_6$ alklyl, or $R^p$ and $R^q$ together with the nitrogen atom they are bonded to form a 4-15 membered heterocycle.

"Alkyl" refers to monovalent saturated aliphatic hydrocarbyl groups having from 1 to 10 carbon atoms and, in some embodiments, from 1 to 6 carbon atoms. "$C_{x-y}$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" refers to divalent saturated aliphatic hydrocarbyl groups having from 1 to 10 carbon atoms and, in some embodiments, from 1 to 6 carbon atoms. "$C_{u-v}$ alkylene" refers to alkylene groups having from u to v carbon atoms. The alkylidene and alkylene groups include branched and straight chain hydrocarbyl groups. For example, "$C_{1-6}$ alkylene" includes methylene, ethylene, propylene, 2-methypropylene, pentylene, and the like. "Heteroalkylene" refers to an alkylene wherein a chain carbon atom is replaced with a heteroatom such as O, S, N, or P, or a heteroatom containing substituent.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $C_{x-y}$ alkenyl refers to alkenyl groups having from x to y carbon atoms and is meant to include, for example, ethenyl, propenyl, 1,3-butadienyl, and the like. "Alkenylene" refers to a divalent alkenyl radical having the appropriate hydrogen content. "Heteroalkenylene" refers to an alkenylene wherein a chain carbon atom is replaced with a heteroatom such as O, S, N, or P, or a heteroatom containing substituent.

"Phosphoramidate alkylating agent" refers to an alkylating agent comprising one or more $Z^5$—$X^5$—$Y^5$ moieties bonded to an —O—P($Z^1$) moiety, where $Z^5$ is a heteroatom such as nitrogen, sulfur or oxygen, $X^5$ is optionally substituted ethylene, $Y^5$ is halo or another leaving group, or $Z^5$—$X^5$—$Y^5$ together form an aziridinyl ($NCH_2CH_2$) moiety, and $Z^1$ is defined as above. Such an alkylating agent can react with a DNA or another nucleic acid, or a protein. In some instances an alkylating agent can cross link a DNA.

"Alkynyl" refers to a linear monovalent hydrocarbon radical or a branched monovalent hydrocarbon radical 2 to 10 carbon atoms and in some embodiments from 2 to 6 carbon atoms or 2 to 4 carbon atoms and containing at least one triple bond. The term "alkynyl" is also meant to include those hydrocarbyl groups having one triple bond and one double bond. For example, $C_{2-6}$ alkynyl includes ethynyl, propynyl, and the like. "Alkynylene" refers to a divalent alkynyl radical having the appropriate hydrogen content. "Heteroalkynylene" refers to an alkynylene wherein a chain carbon atom is replaced with a heteroatom such as O, S, N, or P, or a heteroatom containing substituent.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring). "Arylene" refers to a divalent aryl radical having the appropriate hydrogen content.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "Cycloalkylene" refers to a divalent cycloalyl radical having the appropriate hydrogen content.

"Ether" refers to a $C_1$-$C_6$ alkyl group substituted with 1-3 $C_1$-$C_6$ alkoxy groups, wherein alkoxy refers to —O-alkyl.

"Halo" refers to one or more of fluoro, chloro, bromo, and iodo.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl-2-yl and imidazol5-yl) and multiple ring systems (e.g. imidazopyridyl, benzotriazolyl, benzimidazol-2-yl and benzimidazol-6-yl). For multiple ring systems, including fused, bridged, and spiro ring systems having aromatic and non-aromatic rings, the term "heteroaryl" applies if there is at least one ring heteroatom, and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. The term heteroaryl includes, but is not limited to, acridinyl, azocinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzothienyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazopyridyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isoquinolyl, isothiazolyl, isoxazolyl, naphthyridinyl, octahydroisoquinolinyl, oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. "Heteroarylene" refers to a divalent heteroaryl radical having the appropriate hydrogen content.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom, and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In some embodiment, the heterocyclic groups herein are 3-15 membered, 4-14 membered, 5-13 membered, 7-12, or 5-7 membered heterocycles. In some other embodiment, the heterocycles contain 4 heteroatoms. In some other embodiment, the heterocycles contain 3 heteroatoms. In another embodiment, the heterocycles contain up to 2 heteroatoms. In some embodiments, the nitrogen and/or sulfur atom(s) of the heterocyclic group are optionally oxidized to provide for the N-oxide, sulfinyl, sulfonyl moieties. Heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_{3-10}$) refers to the total number of carbon atoms in the portion of the heterocyclyl group exclusive of the number of heteroatoms. A divalent heterocyclic radical will have the appropriately adjusted hydrogen content.

"Leaving group" refers to a moiety that can be displaced under nucleophilic displacement conditions well known to the skilled artisan. Leaving groups include, without limitation halo and —OSO$_2$—R$^{20}$, where R$^{20}$ is optionally substituted alkyl, aryl, cycloalkyl, heterocyclyl, or heteroaryl.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —SR$^{100}$, —SOR$^{100}$, —SO$_2$R$^{100}$, —NR$^{100}$SO$_2$R$^{100}$, —NR$^{101}$R$^{102}$, —CONR$^{101}$R$^{102}$, —SO$_2$NR$^{101}$R$^{102}$, $C_1$-$C_6$ alkyl, $C_1$-$C_6$ alkoxy, —CR$^{100}$=C(R$^{100}$)$_2$, —CCR$^{100}$, $C_3$-$C_{10}$ cycloalkyl, $C_3$-$C_{10}$ heterocyclyl, $C_6$-$C_{12}$ aryl and $C_2$-$C_{12}$ heteroaryl, or a divalent substituent such as —O—(CH$_2$)—O—, —O—(CH$_2$)$_2$—O—, and, 1-4 methyl substituted version thereof, wherein each R$^{100}$, R$^{101}$, and R$^{102}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; or R$^{101}$ and R$^{102}$ together with the nitrogen atom they are attached to form a 5-7 membered heterocycle; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. Preferably, the substituents are selected from the group consisting of chloro, fluoro, —OCH$_3$, methyl, ethyl, isopropyl, cyclopropyl, —CO$_2$H and salts and $C_1$-$C_6$ alkyl esters thereof, CONMe$_2$, CONHMe, CONH$_2$, —SO$_2$Me, —SO$_2$NH$_2$, —SO$_2$NMe$_2$, —SO$_2$NHMe, —NHSO$_2$Me, —NHSO$_2$CF$_3$, —NHSO$_2$CH$_2$Cl, —NH$_2$, —OCF$_3$, —CF$_3$ and —OCHF$_2$.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Drugs" utilized herein as part of the D moiety includes without limitation, gemcitibine, erlotinib, meturedepa, uredepa, altretamine, imatinib, triethylenemelamine, trimethylolomelamine, chlorambucil, chlornaphazine, estramustine, gefitinib, mechlorethamine, mechlorethamine oxide hydrochloride, melphalan, novembichin, phenesterine, prednimustine, trofosfamide, uracil mustard, carmustine, chlorozotocin, fotemustine, nimustine, ranimustine, dacarbazine, mannomustine, mitobronitol, mitolactol, pipobroman, aclacinomycins, actinomycin, anthramycin, azaserine, bleomycin, cactinomycin, carubicin, carzinophilin, chromomycin, dactinomycin, daunorubicin, daunomycin, 6-diazo-5-oxo-1-norleucine, mycophenolic acid, nogalamycin, olivomycin, peplomycin, plicamycin, porfiromycin, puromycin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, 5-fluorouracil, tegafur, L-asparaginase, pulmozyme, aceglatone, aldophosphamide glycoside, aminolevulinic acid, amsacrine, bestrabucil, bisantrene, defofamide, demecolcine, diaziquone, elfornithine, elliptinium acetate, etoglucid, flutamide, hydroxyurea, interferon-alpha, interferon-beta, interferon-gamma, interleukin-2, lentinan, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, erlotonib, teniposide, tenuazonic acid, triaziquone, 2,2',2"-trichlorotriethylamine, urethan, vinblastine, and vincristine.

"Patient" and "subject" are used interchangeably to refer to a mammal in need of treatment for cancer. Generally, the patient is a human. Generally, the patient is a human diagnosed with cancer. In certain embodiments a "patient" or "subject" may refer to a non-human mammal used in screening, characterizing, and evaluating drugs and therapies, such as, a non-human primate, a dog, cat, rabbit, pig, mouse or a rat.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Solid tumor" refers to solid tumors including, but not limited to, metastatic tumors in bone, brain, liver, lungs, lymph node, pancreas, prostate, skin and soft tissue (sarcoma).

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount may be administered in one or more administrations.

"Treating," "treatment of," or "therapy of" a condition or patient refers to taking steps to obtain beneficial or desired results, including clinical results. For purposes of this invention, beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

"Tumor cells" refers to tumor cells of any appropriate species, e.g., mammalian such as murine, canine, feline, equine or human.

DESCRIPTIVE EMBODIMENTS

Provided herein are compound of formula I as disclosed herein above.

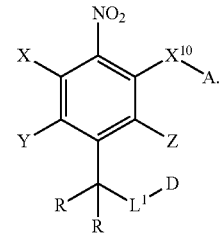

In one embodiment, Z is hydrogen. In another embodiment, X is hydrogen. In another embodiment, Y is hydrogen. In another embodiment, Y is halo.

In some embodiments, each R is hydrogen. In some embodiments, a single R is hydrogen and another R is a non hydrogen substituent as provided herein. In some embodiments, each R is a non-hydrogen substituent as provided herein. In some embodiments, R is $C_1$-$C_6$ alkyl. In some embodiments, R is methyl.

In some embodiments, $R^{40}$, $R^{41}$, and $R^{43}$ are independently hydrogen. In some embodiments, $R^{40}$, $R^{41}$, and $R^{43}$ are independently methyl. In some embodiments, $R^{42}$ is —$CH_2$—$CH_2$—. In some embodiments, $R^{42}$ is —$CH_2$—C(Me)$_2$-. In one embodiment, the carbon atom containing the dimethyl group is bonded to the rest of the linker, $L^1$, which is then bonded to the drug moiety D.

In another embodiment, A is optionally substituted $C_6$-$C_{10}$ aryl. In another embodiment, A is optionally substituted phenyl. In another embodiment, the phenyl is optionally substituted with 1-3, 1-2, or a single substituent selected from halo, —CN, $NO_2$, —$COR^{100}$, —$CO_2R^{100}$, —$OR^{100}$, —$SOR^{100}$, —$SO_2R^{100}$, —$NR^{100}SO_2R^{100}$, —$NR^{101}R^{102}$, —$CONR^{101}R^{102}$, —$SO_2NR^{101}R^{102}$, $C_1$-$C_6$ alkyl, $C_1$-$C_6$ alkoxy, $C_3$-$C_{10}$ cycloalkyl, $C_3$-$C_{10}$ heterocyclyl, $C_6$-$C_{12}$ aryl and $C_2$-$C_{12}$ heteroaryl, or a divalent substituent such as —O—($CH_2$)—O—, —O—($CH_2$)$_2$—O—, wherein each $R^{100}$, $R^{101}$, and $R^{102}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; or and $R^{101}$ and $R^{102}$ together with the nitrogen atom they are attached to form a 5-7 membered heterocycle; wherein each alkyl, cycloalkyl, heterocyclyl, aryl, or heteroaryl is optionally substituted with 1-3 halo, 1-3

$C_1$-$C_6$ alkyl, 1-3 $C_1$-$C_6$ haloalkyl or 1-3 $C_1$-$C_6$ alkoxy groups. In another embodiment, A is biphenyl.

In another embodiment, A is optionally substituted 5-15 membered heteroaryl. In another embodiment, A is optionally substituted pyridyl. In another embodiment, A is optionally substituted benzothiazolyl. In another embodiment, A is quinolinyl.

In another embodiment, A is —N=CR$^1$R$^2$ where R$^1$ and R$^2$ are defined as herein.

In certain embodiments, certain suitable substituents for A is disclosed as part of the specific compounds provided herein below.

In some embodiments, non-limiting examples of V(-) includes halides, an alkyl or an arylsulfonate, a carboxylate, and the likes. An alkyl or an arylsulfonate includes without limitation, or MeSO$_3$— or TsO—. A carboxylate includes without limitation acetate or formate.

In one embodiment, the D moiety is part of: SN-38, irinotecan, topotecan, camptothecin, or such other quinolinyl topoisomerase 1 inhibitor; bendamustine; a vasculature disrupting agent; doxorubicin, daunorubicin, or another anthracycline; pemetrexed; vorinostat; lenalidomide or another thalidomide derivative; ganetespib; docetaxel, paclitaxel, or another taxoid; 17-AAG; 5-FU, gemcitabine, mercaptopurine (6-MP, Purinethol), fluorouracil (5-FU, Adrucil), thioguanine, (6-TG, Thioguanine), cytarabine (Cytosar-U, DepoCyt), floxuridine (FUDR), fludarabine (Fludara), azacytidine (Vidaza), pentostatin (Nipent), cladribine (Leustatin, 2-CdA), gemcitabine (Gemzar), and capecitabine (Xeloda), and such other nucleoside derivatives; abiraterone; imatinib, nilotinib, erlotinib, sorafenib, sunitinib, gefitinib, lapatinib, dasatinib, bosutinib, ponatinib, ibrutinib, afatinib, dabrafenib, cabozantinib, regorafenib, pazopanib, axitinib, ruxolitinib, crizotinib, vemurafenib, vandetanib, In certain embodiments, the D moiety is part of certain drugs as illustrated herein below.

In one embodiment, L$^1$ is

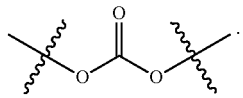 [SMILES: *OC(=O)O*]

In another embodiment, L$^1$ is:

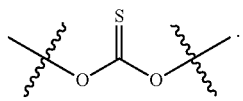 [SMILES: *OC(=S)O*]

In another embodiment, L$^1$ is:

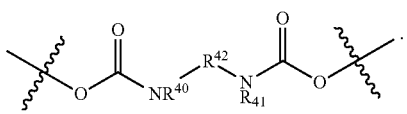

In another embodiment, L$^1$ is:

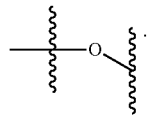

In another embodiment, L$^1$ is:

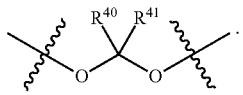

In another embodiment, L$^1$ is:

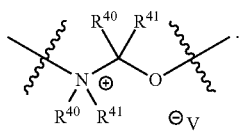

In another embodiment, L$^1$ is:

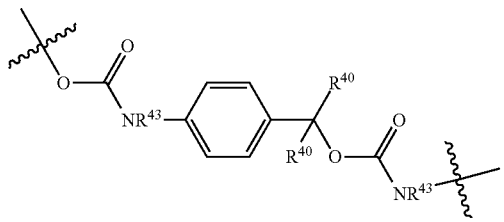

In another embodiment, L$^1$ is:

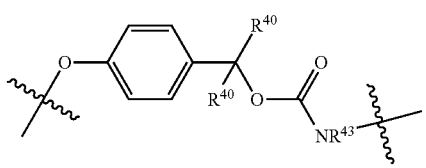

In another embodiment, L$^1$ is:

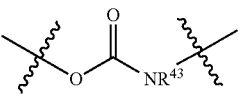

In another embodiment, L$^1$ is a bond. In another embodiment, L$^1$ is —O—C(R$^{40}$R$^{41}$)$_2$—. In another embodiment, L$^1$ is:

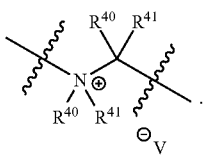

In one embodiment, provide herein is a compound of formula 1A-1:

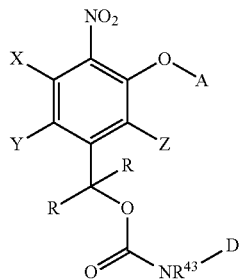

1A-1 wherein the variables are defined as in any aspect and embodiment above. As to D, HNR$^{43}$-D is the cytotoxic agent containing a primary or a secondary amino group, In one embodiment, provide herein is a compound of formula 1A-2:

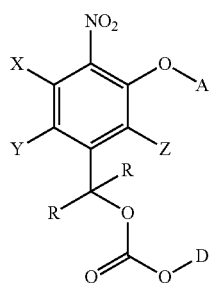

1A-2 wherein the variables are defined as in any aspect and embodiment above. As to D, HO-D is cytotoxic agent containing at least one hydroxyl group.

In one embodiment, provide herein is a compound of formula 1A-3:

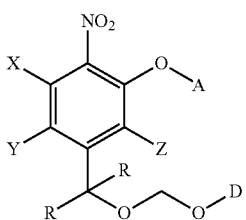

1A-3 wherein the variables are defined as in any aspect and embodiment above. As to D, HO-D is cytotoxic agent containing at least one hydroxyl group.

In one embodiment, provided herein is a compound of formula 1A-4:

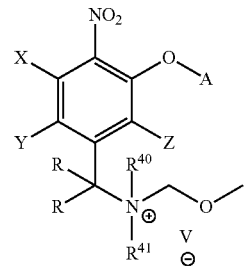

1A-4 wherein the variables are defined as in any aspect and embodiment above, and as to D, HO-D is cytotoxic agent containing at least one hydroxyl group.

In one embodiment, provide herein is a compound of formula 1A-5

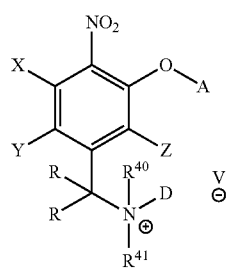

1A-5 wherein the variables are defined as in any aspect and embodiment above.

In one embodiment, provide herein is a compound of formula 1A-6

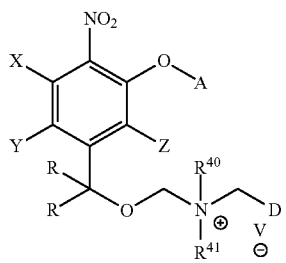

1A-6 wherein the variables are defined as in any aspect or embodiment above and D is a drug containing a secondary nitrogen atom, where that secondary nitrogen atom is bonded to the methylene group as shown above.

In one embodiment, provide herein is a compound of formula 1A-7

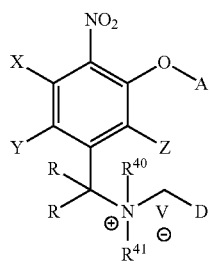

IA-7 wherein the variables are defined as in any aspect or embodiment above and D is a drug containing a secondary nitrogen atom, where that secondary nitrogen atom is bonded to the methylene group as shown above.

In one embodiment, provide herein is a compound of formula 1A-8

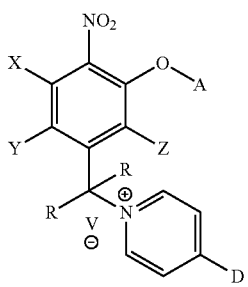

IA-8 wherein the variables are defined as in any aspect or embodiment above and D together with the pyridine moiety attached to it is a drug, where that nitrogen atom is bonded to the methylene group as shown above.

In one embodiment, provide herein is a compound of formula 1A-9

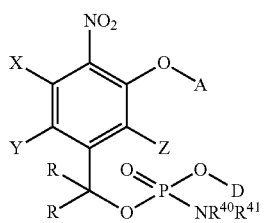

IA-9 wherein the variables are defined as in any aspect or embodiment above and D is a drug containing hydroxyl group.

In one embodiment, provide herein is a compound of formula 1A-10

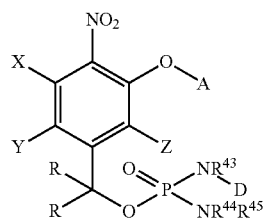

IA-10 wherein the variables are defined as in any aspect and embodiment above. As to D, $HNR^{43}$-D is the cytotoxic agent containing a primary or a secondary amino group.

In other embodiments, the —O-A moiety as shown herein above, is replaced with another —$X^{10}$-A moiety as provided herein.

In certain embodiments, the D moiety is part of certain drugs as illustrated herein below.

In one embodiment, provided herein is a compound of formula:

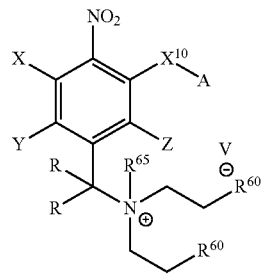

wherein each $R^{60}$ independently is halo or an optionally substituted alkyl or aryl sulfonate, and $R^{65}$ is $C_1$-$C_6$ alkyl, preferably methyl.

In one embodiment, provided herein is a compound of formula:

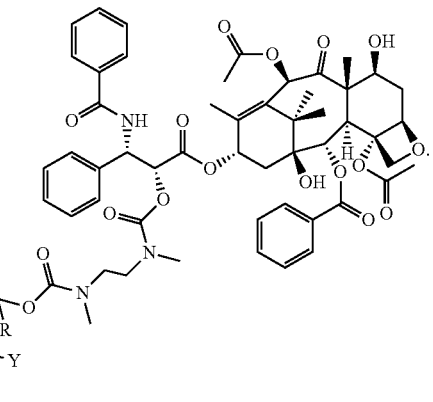

In one embodiment, the compound provided herein is of formula:

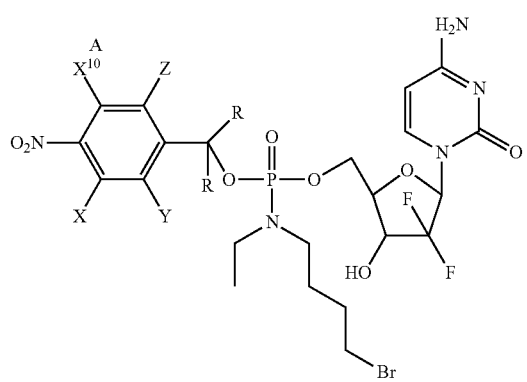

In one embodiment, the compound provided herein is of formula:

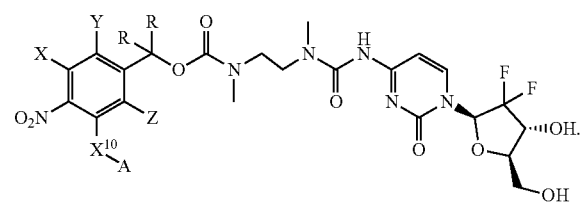

In one embodiment, the compound provided herein is of formula:

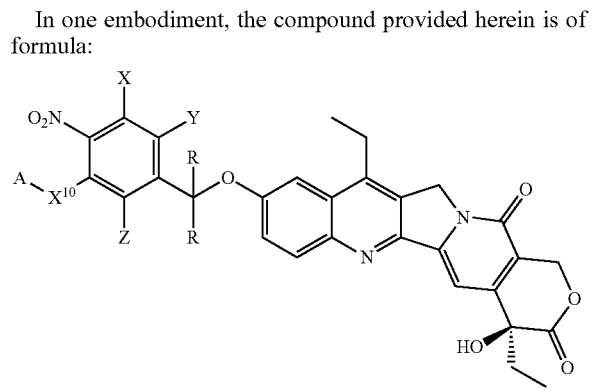

In one embodiment, the compound provided herein is of formula:

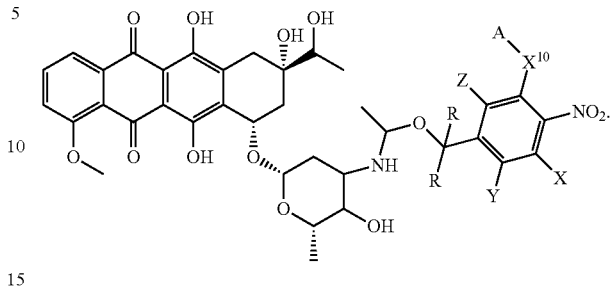

In one embodiment, the compound provided herein is of formula:

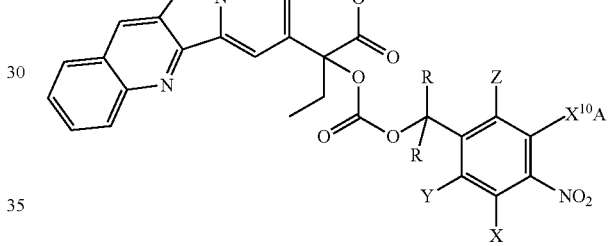

In another embodiment, provided herein is a compound disclosed below or a pharmaceutically acceptable salt or a solvate of each thereof. In one embodiment, the compounds include a taxoid as an anticancer agent:

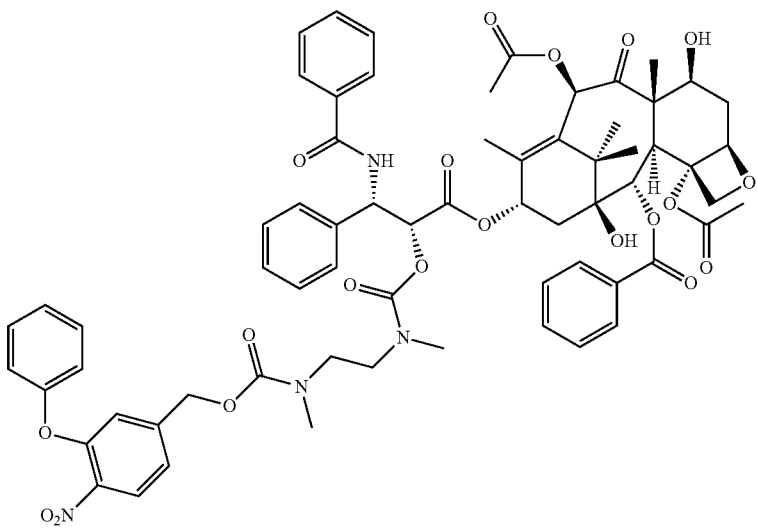

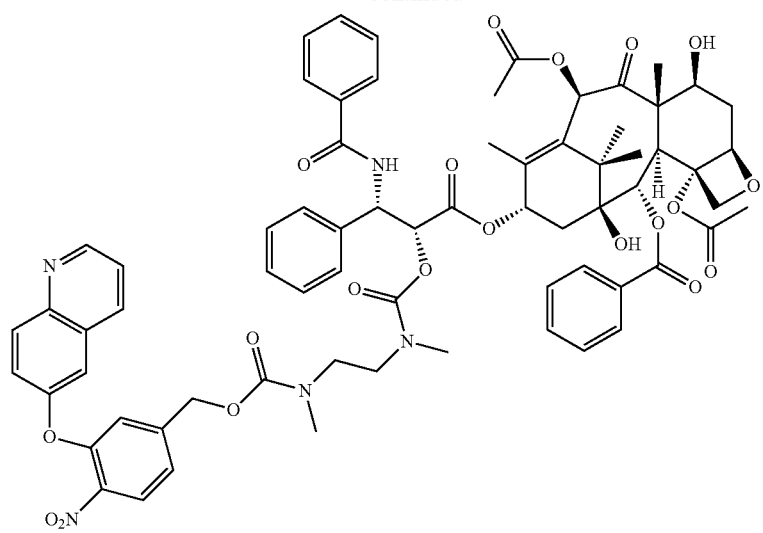
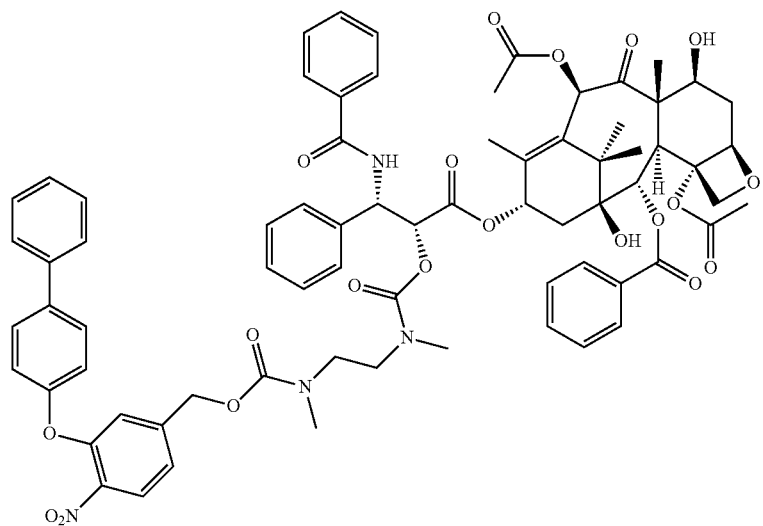
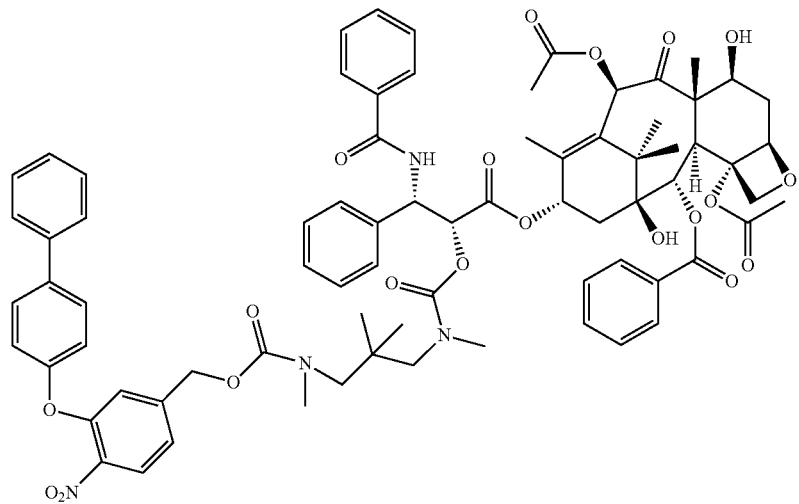

-continued
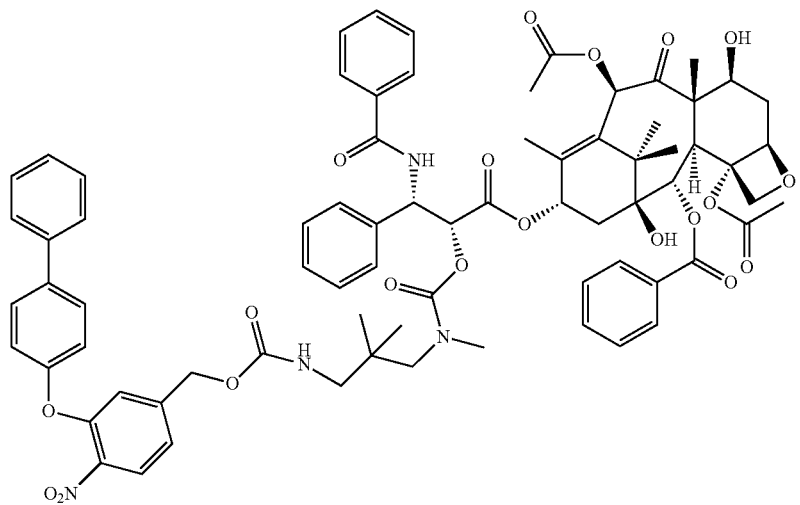
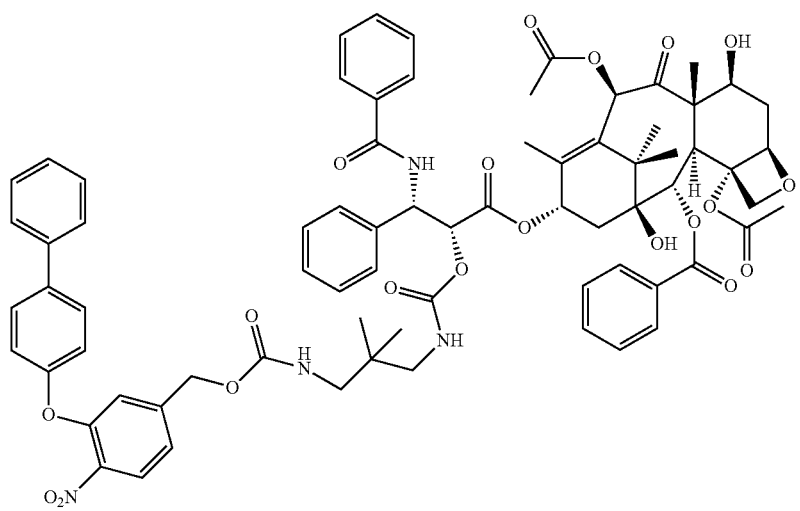
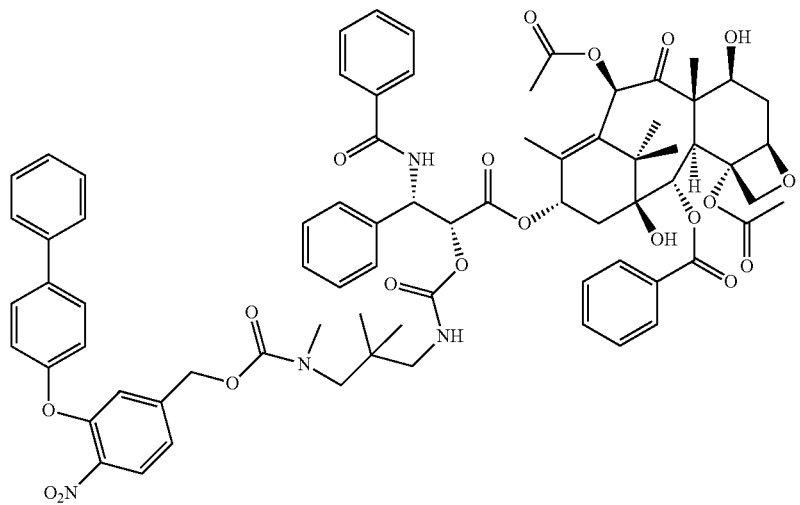

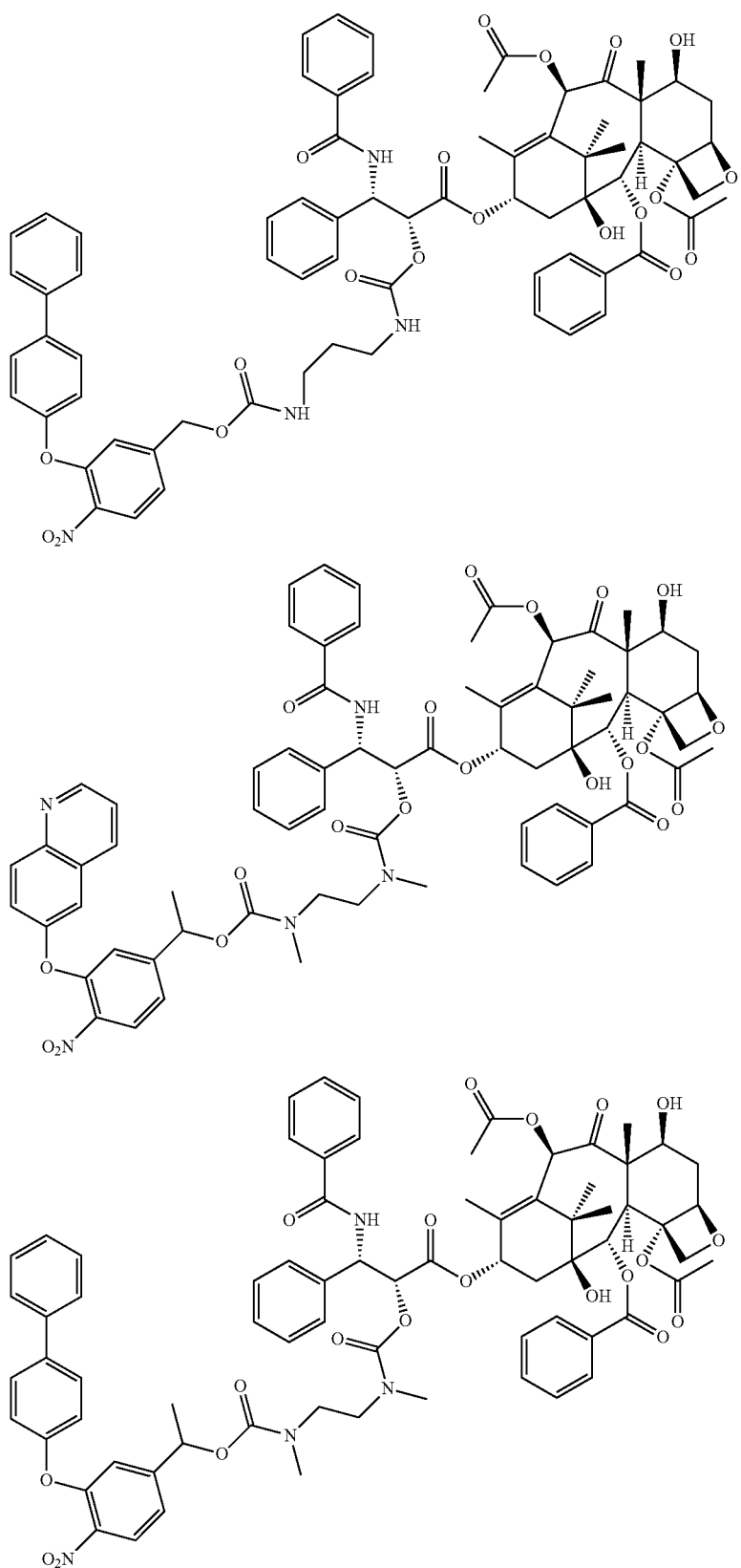

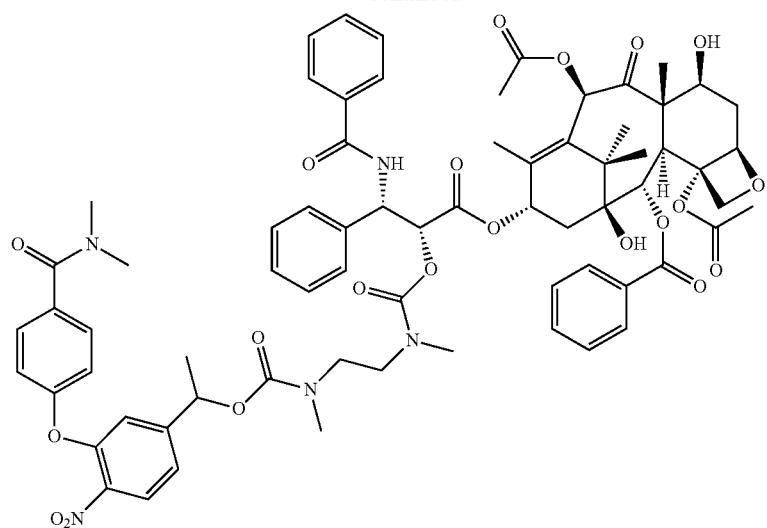
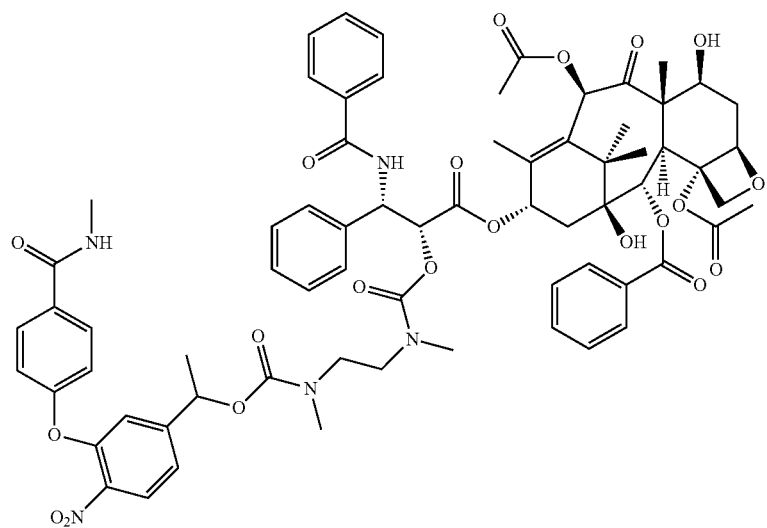
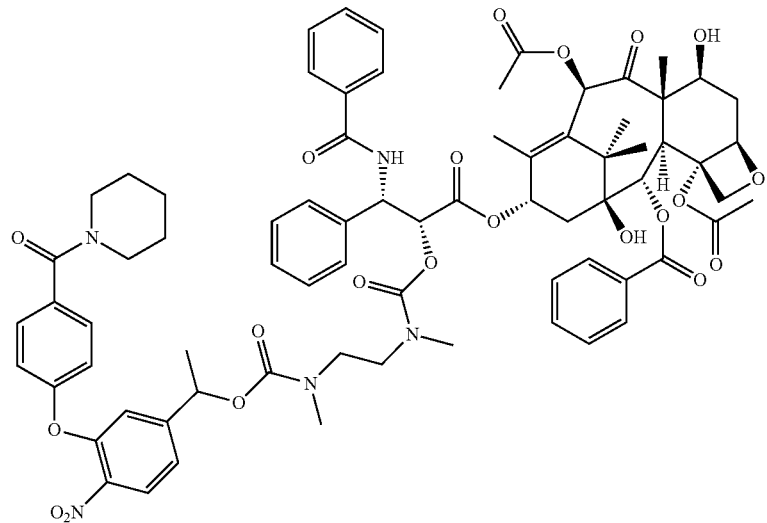

-continued
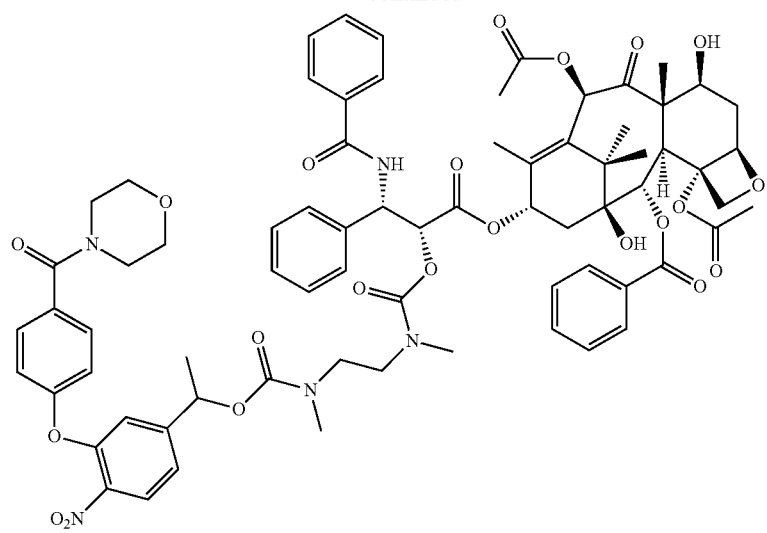
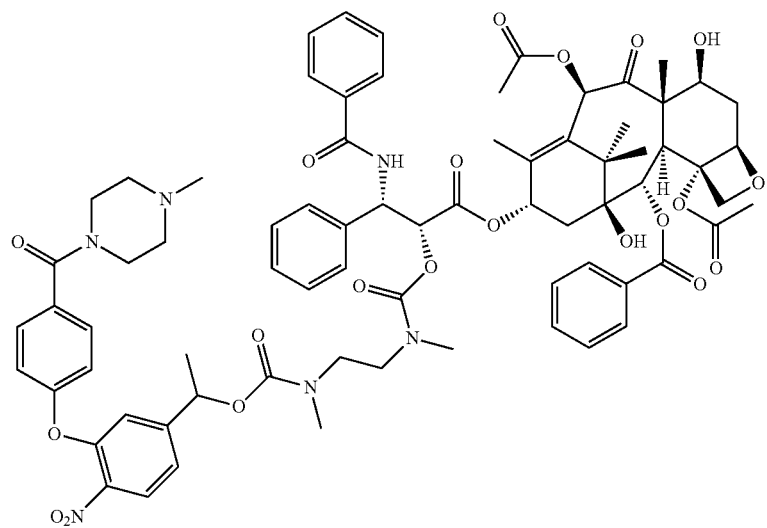
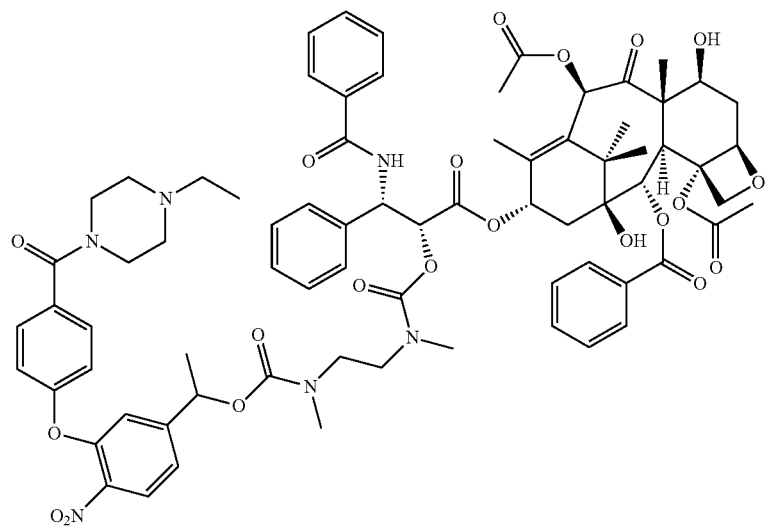

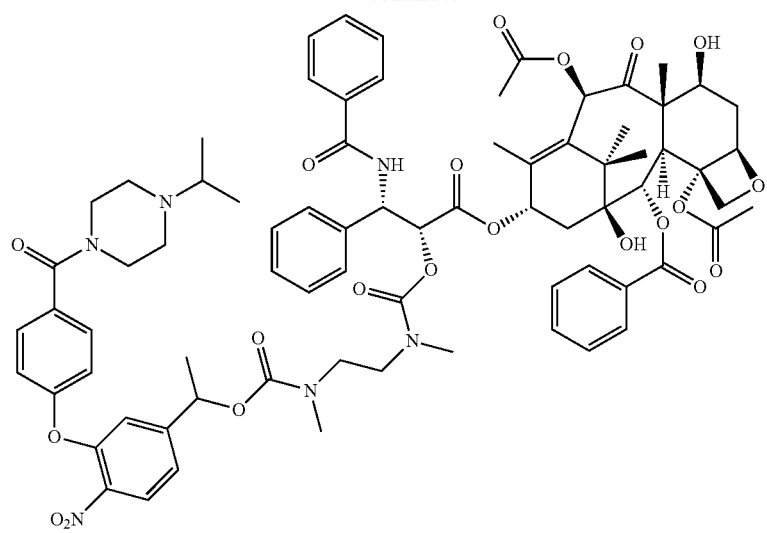
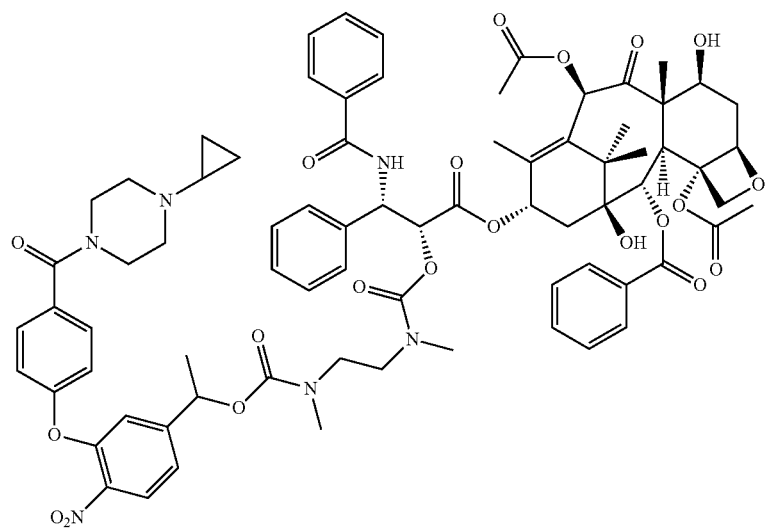
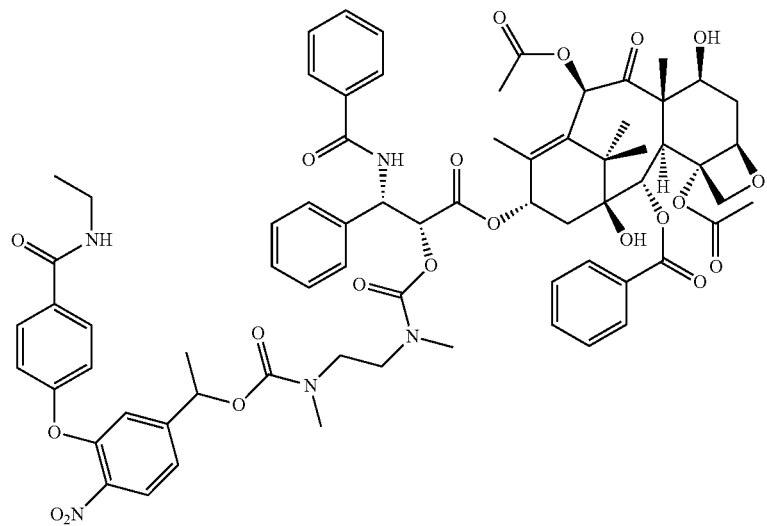

-continued
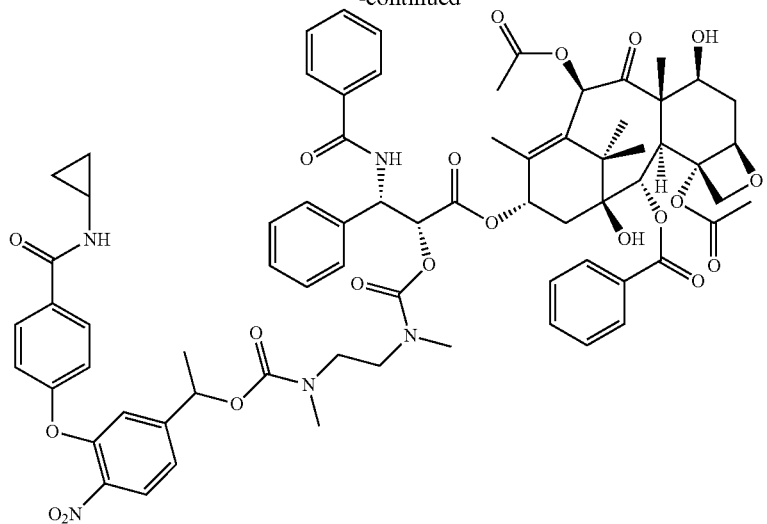
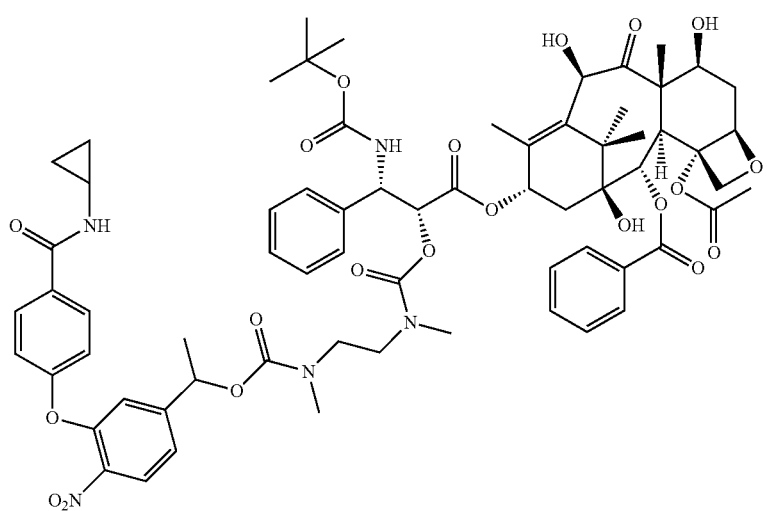
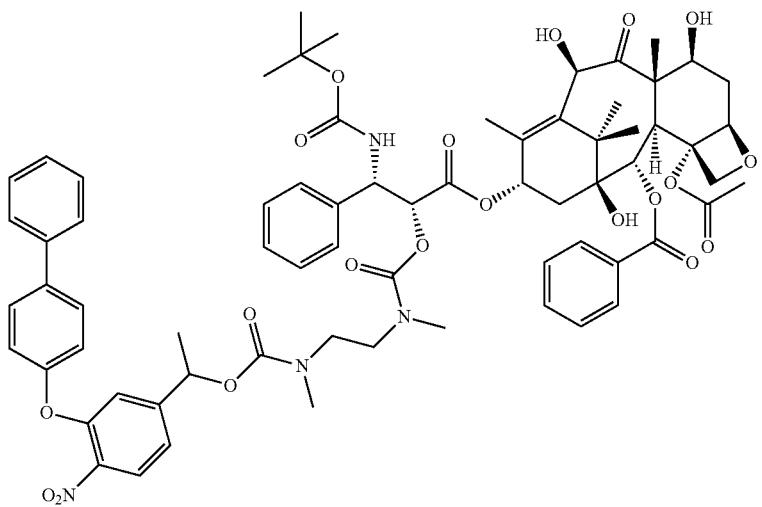

In one embodiment, the compounds include a nucleoside anticancer agent:
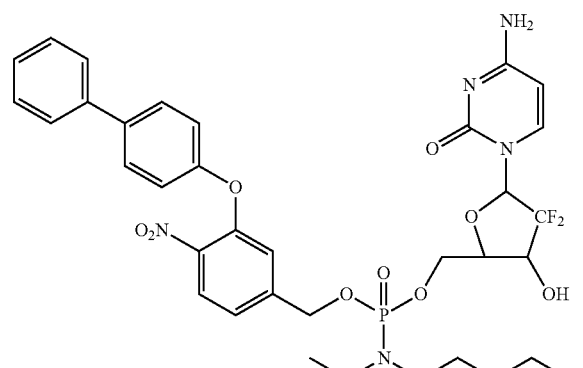
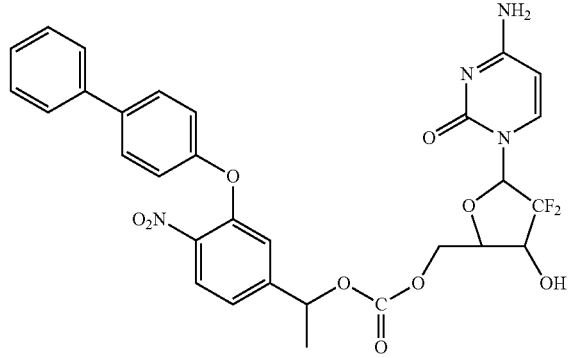
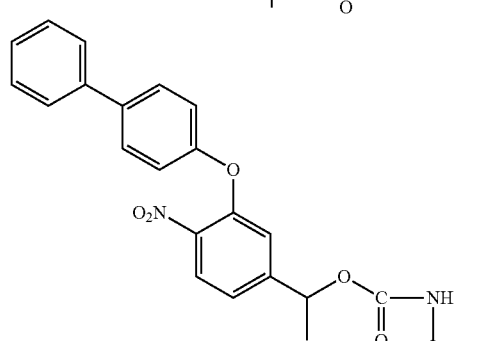
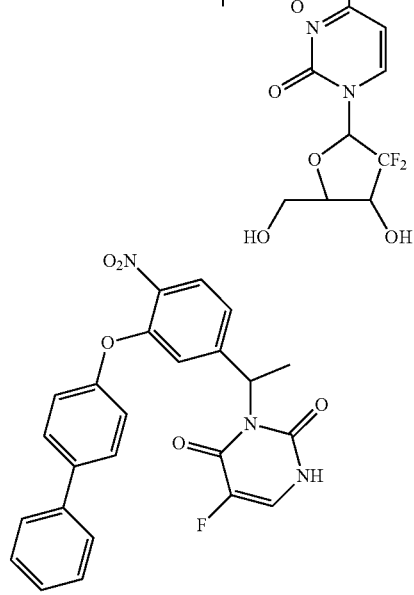
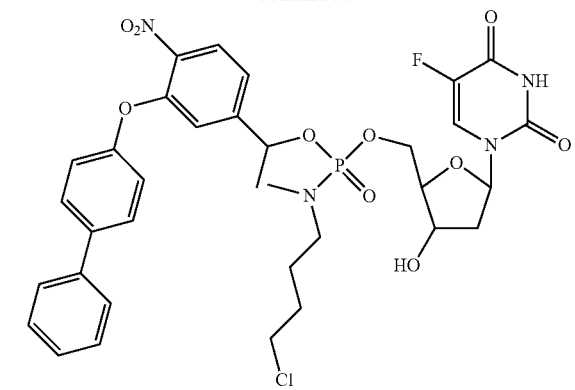
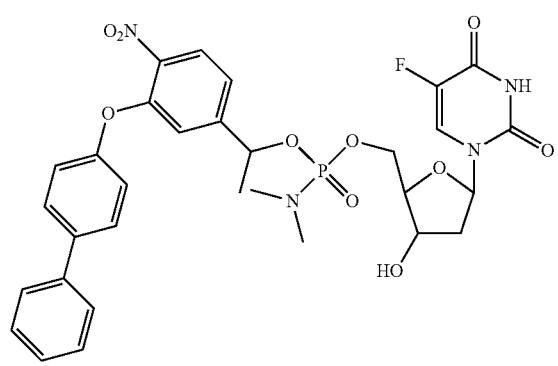
In one embodiment, the compounds include an anthracycline derivative such as shown below as an anticancer agent:
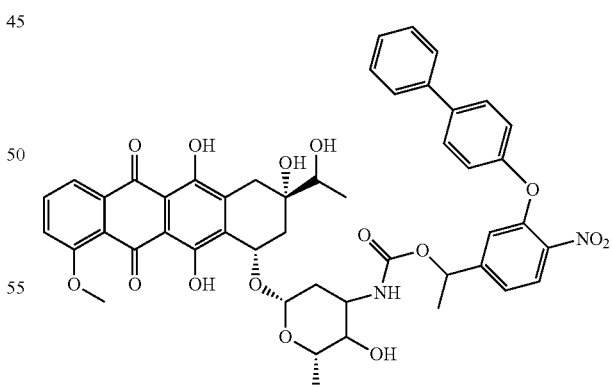
In one embodiment, the compounds include a camptothecin derivative such as SN-38 as an anticancer agent and such other compounds:

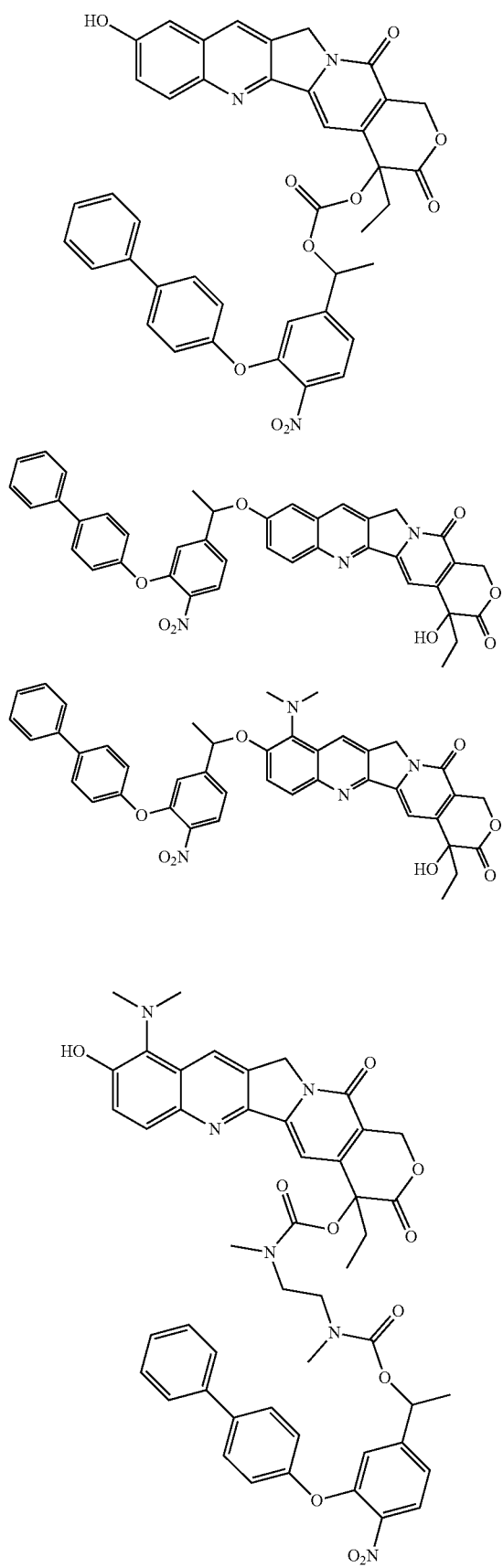
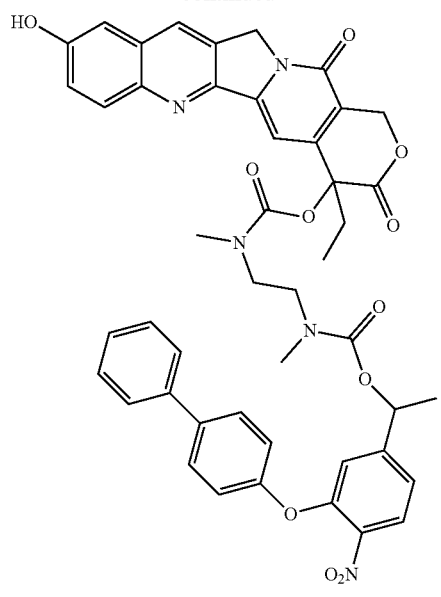 [SMILES: CCC1(OC(=O)N(C)CCN(C)C(=O)OC(C)c2ccc([N+](=O)[O-])c(Oc3ccc(-c4ccccc4)cc3)c2)C(=O)OCc2c1cc1n(c2=O)Cc2cc3cc(O)ccc3nc2-1]
In one embodiment, the compound includes an alkylating anticancer agent such as mechlorethamine:
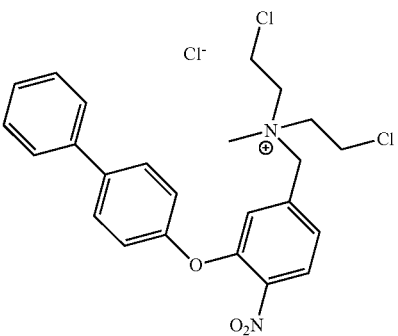 [SMILES: C[N+](CCCl)(CCCl)Cc1ccc([N+](=O)[O-])c(Oc2ccc(-c3ccccc3)cc2)c1 ; [Cl-]]
In one embodiment, the compound includes etoposide as an anticancer agent:
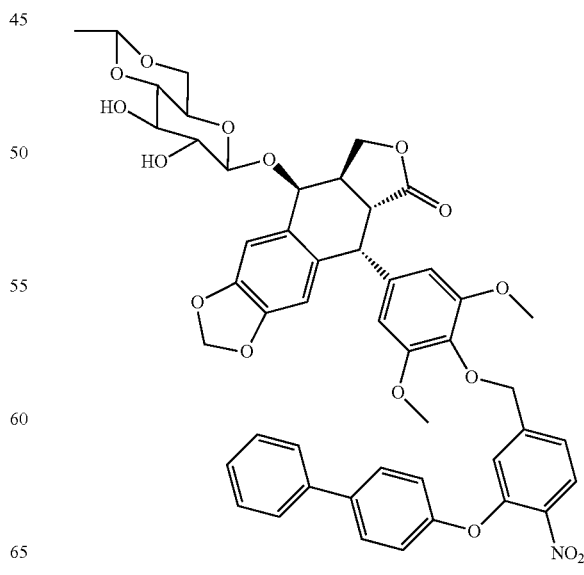

In one embodiment, the compounds include the tubulin targeting agents, tasidotin and auristatin as an anticancer drug:
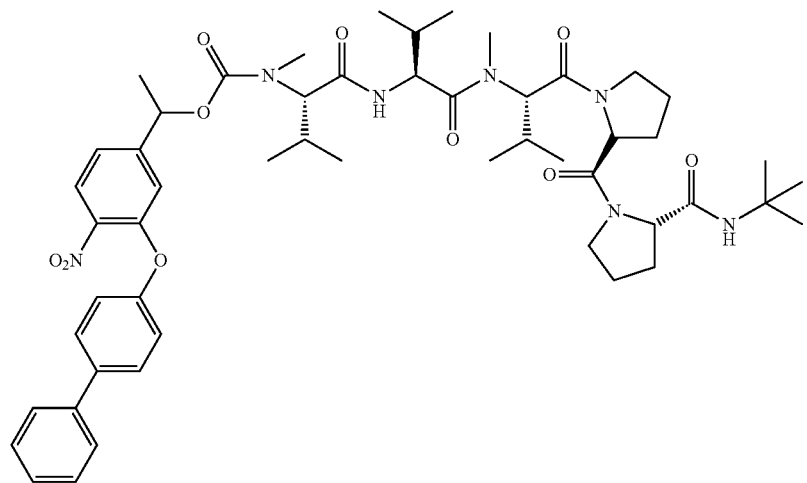
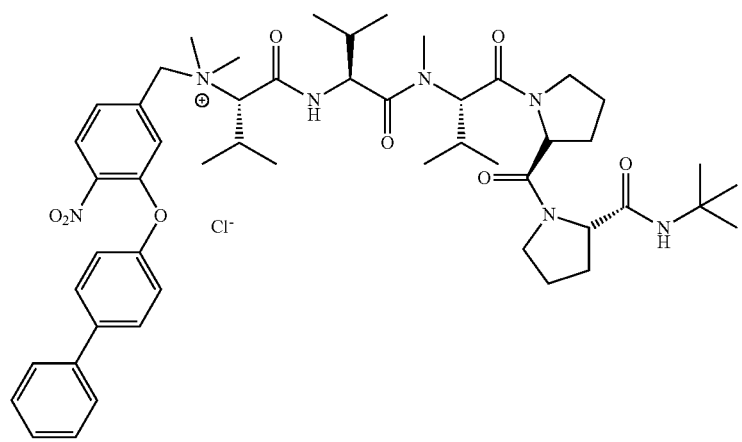
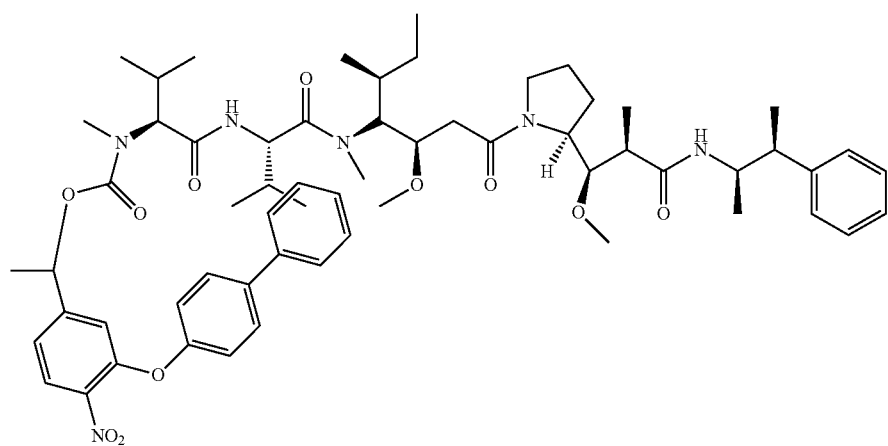

In one embodiment, the compounds include a kinase inhibitor as an anticancer agent:

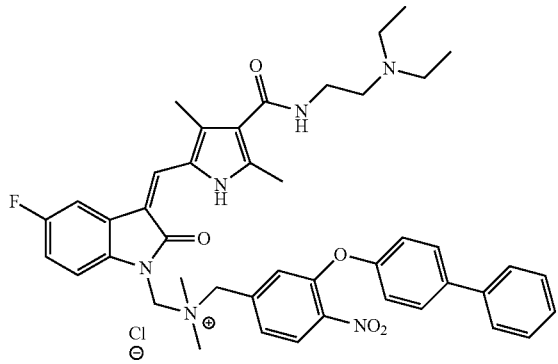

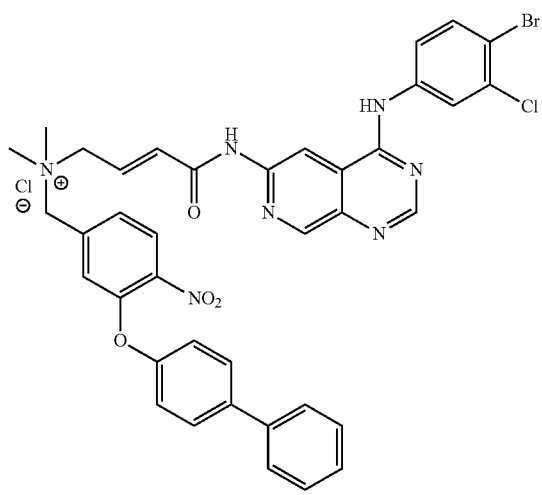

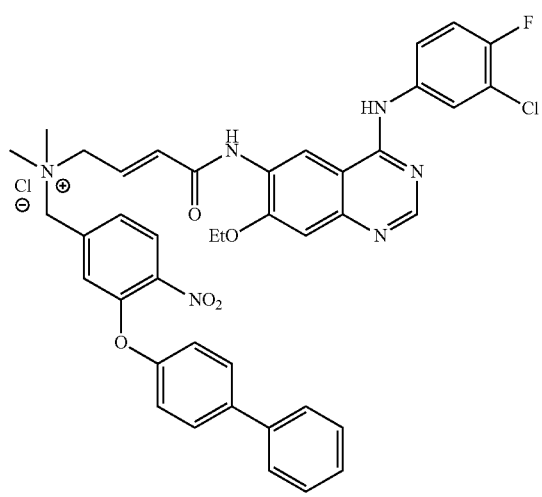

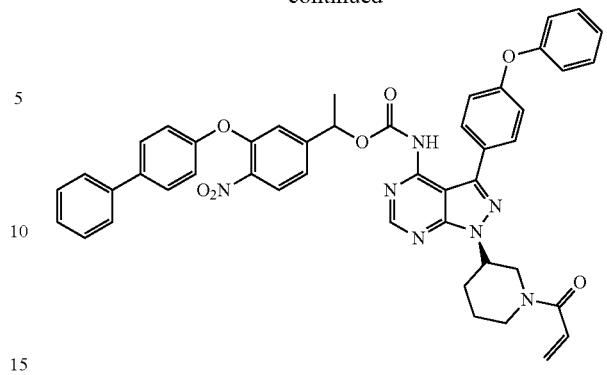

In one embodiment, the compounds include prodrugs of other irreversible kinase inhibitors described in Qingsong Liu et al, Chem Biol., 2013, 20(2), page 146-159.

Examples of compounds provided herein also include those disclosed in the examples section below.

In another aspect, provided herein is a process of preparing a compound of formula I comprising contacting a compound of formula II:

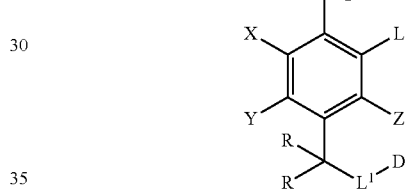

wherein L is a leaving group, with a compound of formula III:

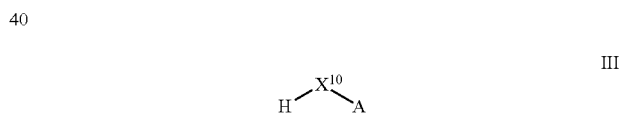

and optionally a base to provide a compound of formula I, wherein the remaining variables are defined in any aspect or embodiment, as above.

In one embodiment, L is halo. In another embodiment, L is F. In another embodiment, $X^{10}$ is O. In another embodiment, Z is hydrogen. In another embodiment, X is hydrogen. In another embodiment, Y is hydrogen. In another embodiment, Y is halo. In one embodiment, the base is a strong, non-nucleophilic base, as is well known to the skilled artisan, In one embodiment, the base is a hydride base.

Illustrative and non-limiting method of making the compounds provided herein are shown below:

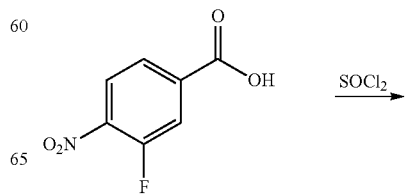

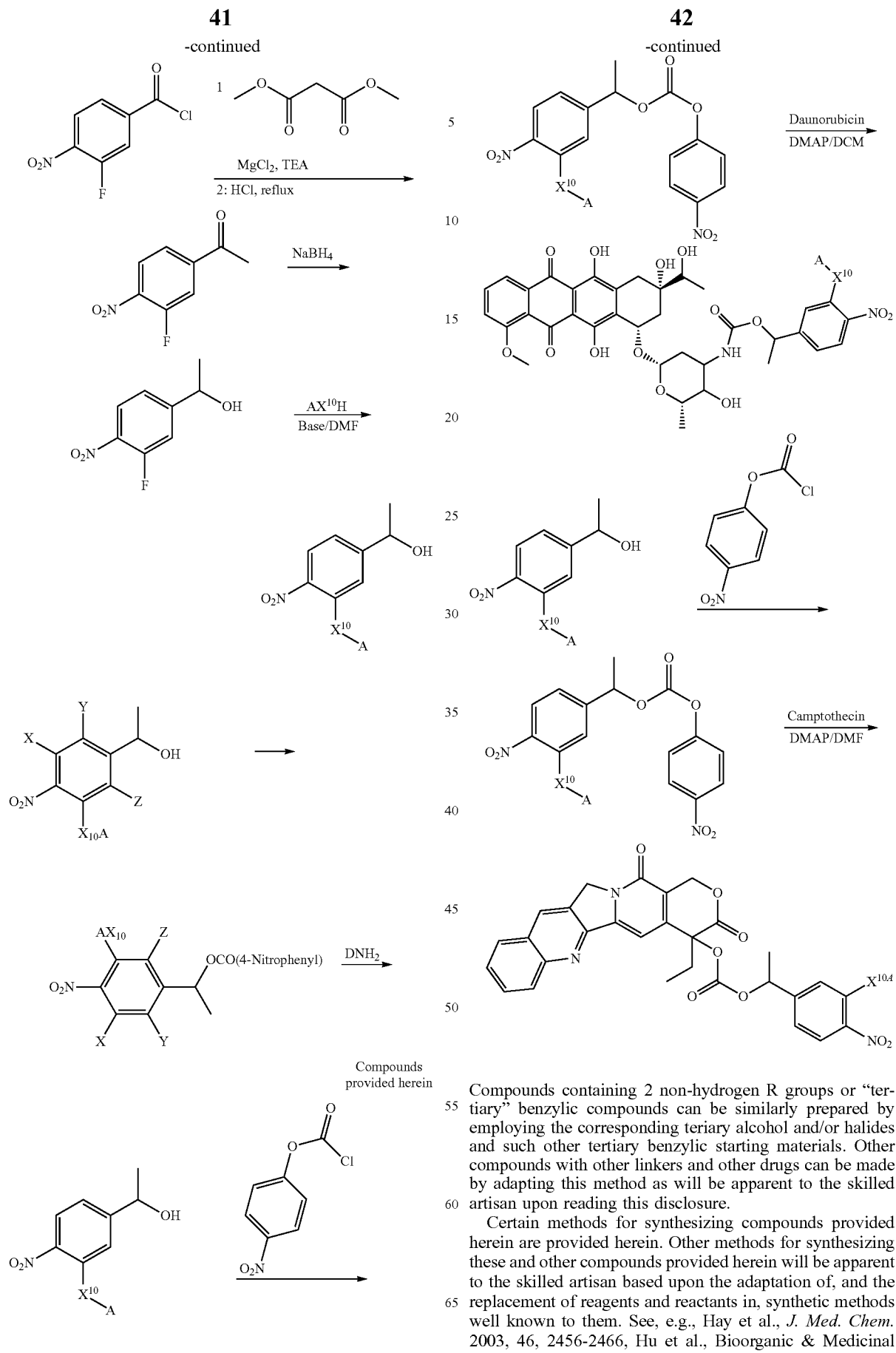

Compounds containing 2 non-hydrogen R groups or "tertiary" benzylic compounds can be similarly prepared by employing the corresponding teriary alcohol and/or halides and such other tertiary benzylic starting materials. Other compounds with other linkers and other drugs can be made by adapting this method as will be apparent to the skilled artisan upon reading this disclosure.

Certain methods for synthesizing compounds provided herein are provided herein. Other methods for synthesizing these and other compounds provided herein will be apparent to the skilled artisan based upon the adaptation of, and the replacement of reagents and reactants in, synthetic methods well known to them. See, e.g., Hay et al., *J. Med. Chem.* 2003, 46, 2456-2466, Hu et al., Bioorganic & Medicinal Chemistry Letters 21 (2011) 3986-3991, and WO 2008151253. Starting materials useful for preparing the compounds provided herein are commercially available or can be prepared following routine methods. The reactions are commonly carried out in an inert solvent and heated if necessary. The skilled artisan will readily appreciate that certain reactions may require the use of a protecting group. Protecting groups are well known to the skilled artisan and described, e.g., in Greene's Protective Groups in Organic Synthesis. Peter G. M. Wuts and Theodora W. Greene, 4th Edition or a later edition, John Wily & Sons, Inc., 2007. The reaction products may be separated following routine methods such as crystallization, precipitation, distillation, and/or chromatography. The purity of a compound or an intermediate can be ascertained using well known methods such as $^1$H-NMR, HPLC, TLC, and the likes.

EXAMPLES

Example 1

Synthesis of the compounds provided herein

A.

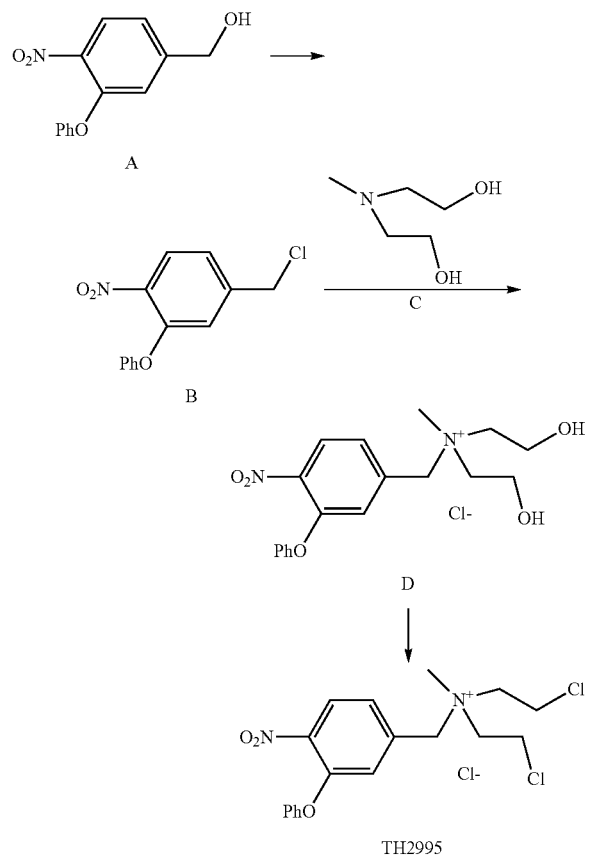

Compound B

A solution of Compound A (110 mg) in 5 ml of $SOCl_2$ was heated at 90° C. for 3 hrs. Then the solvent was removed under vacuum. The residue was resolved in toluene (5 ml) and the solvent was removed again to get Compound B (112 mg) without further purification.

Compound D

A solution of Compound B (80 mg), compound C (2 mL) in ACN (acetonitrile, 2 ml) was heated at 80° C. for overnight. The solvent was removed under vacuum. Chromatography of the residue on silica gel (ACN:$H_2O$=80:20 (V/V)) afforded 65 mg of Compound D.

TH2995

A solution of Compound D (60 mg) in 5 ml of $SOCl_2$ was heated at 90° C. for 4 hrs. Then the solvent was removed under vacuum. Chromatography of the residue on silica gel (AcOEt:MeOH=90:10 (V/V)) afforded 50 mg of TH2995. 1HNMR ($CDCl_3$+$CD_3OD$): 7.94 (1H), 7.38 (2H), 7.18 (2H), 7.04 (3H), 4.70 (2H), 3.96 (3H), 3.56 (4H), 2.86 (4H).

B.

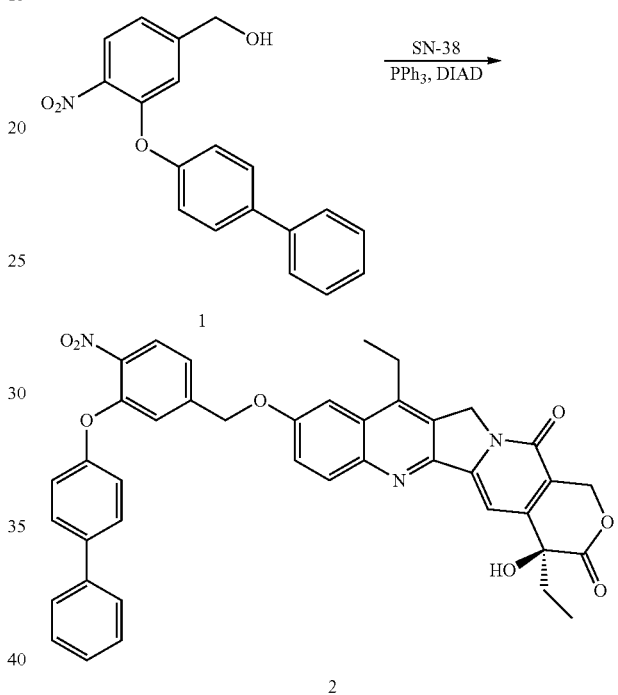

To a suspension of Compound 1 (0.16 g, 0.5 mmol), SN-38 (0.23 g, 0.6 mmol) and $PPh_3$ (0.26 g, 1 mmol) in THF (5 mL) was added DIAD (0.2 g, 1 mmol) at 0° C. The reaction mixture was allowed to warm to room temperature and stirred overnight, purified by flash chromatography on silica gel to yield compound 2. $^1$H NMR (DMSO-d6) δ 8.16 (1H, d, J=9.2 Hz), 8.08 (1H, d, J=9.2 Hz), 7.62-7.52 (6H, m), 7.42 (2H, t, J=8 Hz), 7.34-7.3 (2H, m), 7.27 (1H, s), 7.07 (2H, d, J=8.4 Hz), 6.48 (1H, s), 5.49 (2H, s), 5.43 (2H, s), 5.22 (2H, s), 3.1 (2H, q, J=7.6 Hz), 1.87 (2H, m), 1.18 (3H, t, J=7.6 Hz), 0.877 (3H, t, J=7.2 Hz), m/z (ESI) 696.5 ($M^+$+H).

C.

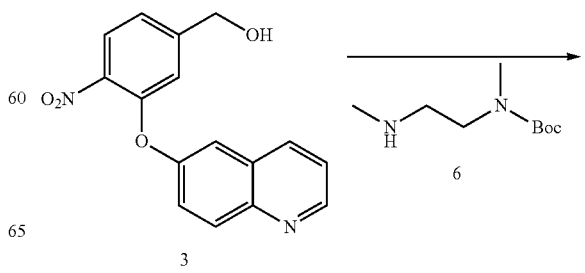

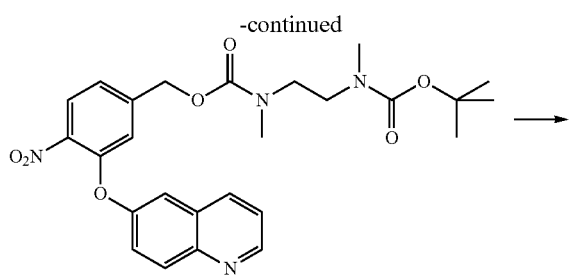

4

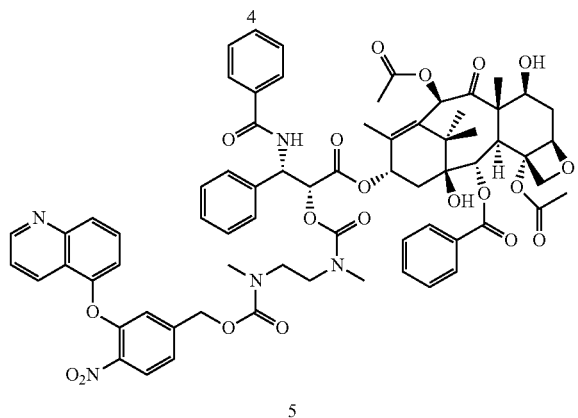

5

To a solution of alcohol 3 (0.6 g, 2 mmol) in DCM (10 mL) was added triethylamine (0.57 mL, 4 mmol) and p-NCF (0.6 g, 3 mmol) at 0° C. under argon. The reaction mixture was allowed to warm to room temperature and stirred overnight. The reaction mixture was washed with water, saturated NaHCO$_3$ and brine. The organic layer was dried over Na$_2$SO$_4$, concentrated under reduced pressure. The residue was purified by chromatography on silica gel to produce the desired PNP carbonate. To the PNP carbonate in THF (10 mL) was added amine 6 (0.38 g, 2 mmol), DIPEA (0.5 mL, 3 mmol) and DMAP (0.1 g) and the solution was stirred at room temperature for 2 hours. The solution was concentrated under reduced pressure and the residue was purified by flash chromatography on silica gel to give compound 4. $^1$H NMR (CDCl$_3$) δ 8.9 (1H, s), 8.16 (1H, d, J=8.4 Hz), 8.1-8.0 (2H, m), 7.52 (1H, dd, J=9, 2.6 Hz), 7.43 (1H, dd, J=8, 4.2 Hz), 7.36-7.3 (1H, m), 7.07 (1H, s), 7.03 (1H, s), 5.11 (2H, s), 3.4-3.1 (4H, m), 3.0-2.7 (6H, m), 1.42 (9H, s), m/z (ESI) 511.2 (M$^+$+H).

To the solution of compound 4 (150 mg, 0.3 mmol) was added a solution of HCl (4 M in dioxane, 1 mL) and the mixture was stirred for 3 hours at ambient temperature. The solvent was removed under reduced pressure to obtain the crude amine salt which was used directly in the following reaction. m/z (ESI) 411.1 (M$^+$+H).

The amine salt was suspended in CH$_2$Cl$_2$ (2 mL), cooled to 0° C. and phosgene (15% in toluene, 0.26 mL, 0.36 mmol) was added followed by addition of triethylamine (0.14 mL, 1 mmol). After 1 hour, Paclitaxel (0.17 g, 0.2 mmol) was added to the reaction mixture followed by addition of DMAP (0.12 g, 1 mmol). The reaction mixture was allowed to warm to room temperature and stirred overnight. The solution was concentrated under reduced pressure and the residue was purified by flash chromatography on silica gel gave compound 5. m/z (ESI) 1290.7 (M$^+$+H).

D.

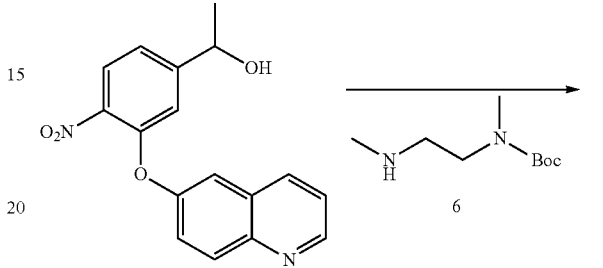

7

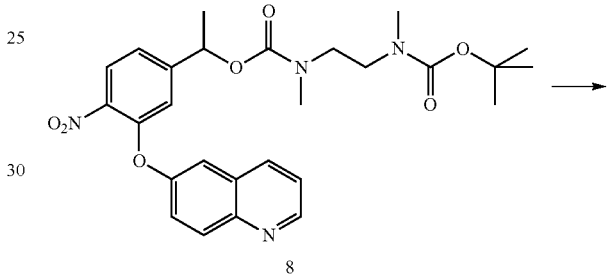

8

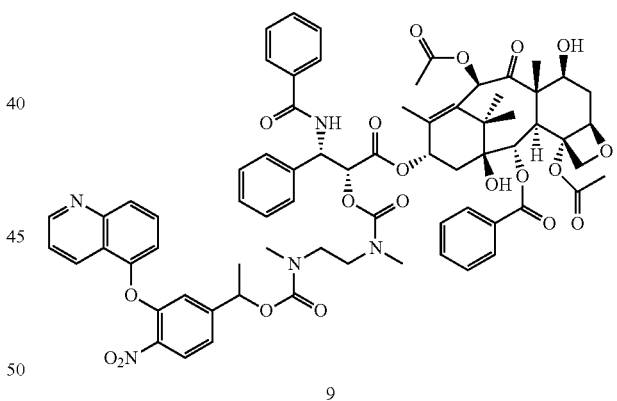

9

Starting from Alcohol 7, compound 9 was prepared. m/z (ESI) 1305.2 (M$^+$+H).

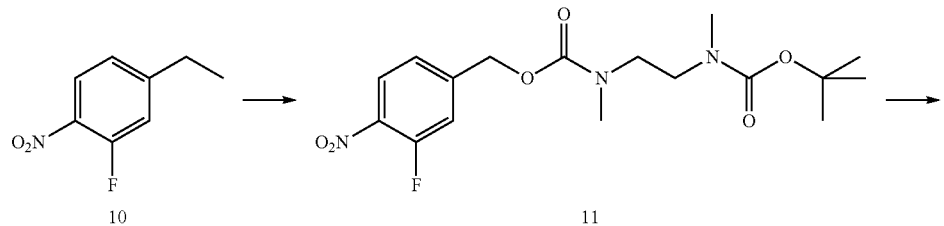

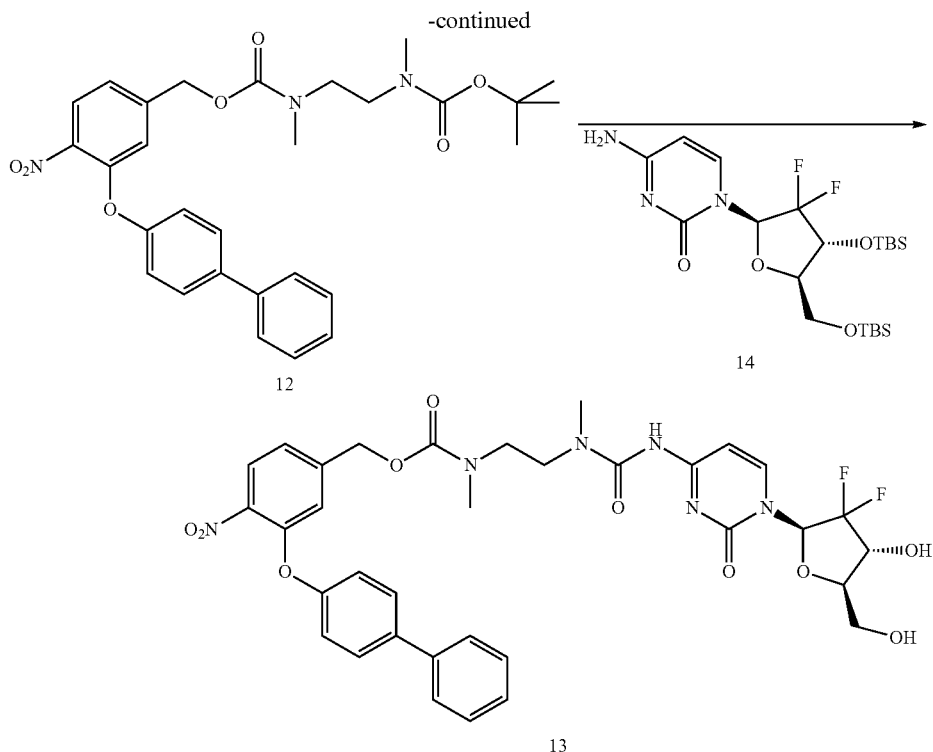

To a solution of alcohol 10 (0.5 g, 3 mmol) in DCM (15 mL) was added triethylamine (0.85 mL, 6 mmol) and p-NCF (0.9 g, 4.5 mmol) at 0° C. under argon. The reaction mixture was allowed to warm to room temperature and stirred overnight. The reaction mixture was washed with water, saturated NaHCO$_3$ and brine. The organic layer was dried over Na$_2$SO$_4$ and concentrated under reduced pressure. The residue was purified by chromatography on silica gel to produce the desired PNP carbonate. To the PNP carbonate in THF (10 mL) was added amine 6 (0.57 g, 3 mmol), DIPEA (0.75 mL, 4 mmol) and DMAP (0.1 g) and the solution was stirred at room temperature for 2 hours. The solution was concentrated under reduced pressure and the residue was purified by flash chromatography on silica gel to give compound 11. $^1$H NMR (CDCl$_3$) δ 8.12-8.04 (1H, m), 7.38-7.2 (2H, m), 5.19 (2H, s), 3.5-3.3 (4H, m), 3.1-2.8 (6H, m), 1.45 (9H, s).

The mixture of compound 11 (0.58 g, 1.5 mmol), K$_2$CO$_3$ (0.41 g, 3 mmol) and 4-Phenylphenol (0.38 g, 2.25 mmol) in DMF (5 mL) was stirred at room temperature overnight. The reaction mixture was diluted with EtOAc and washed with water, brine. The organic layer was dried over Na$_2$SO$_4$ and concentrated under reduced pressure. The residue was purified by chromatography on silica gel to produce compound 12. $^1$H NMR (CDCl$_3$) δ 7.99 (1H, d, J=8.4 Hz), 7.64-7.54 (4H, m), 7.45 (2H, t, J=7.6 Hz m), 7.36 (1H, t, J=7.6 Hz), 7.2-7.15 (1H, m), 7.13 (2H, d, J=8.8 Hz), 7.03 (1H, s), 5.1 (2H, m), 3.5-3.2 (4H, m), 3.0-2.7 (6H, m), 1.42 (9H, s), m/z (ESI) 536.4 (M$^+$+H).

To the solution of compound 12 (150 mg, 0.3 mmol) was added a solution of HCl (4 M in dioxane, 1 mL) and the mixture was stirred for 3 hours at ambient temperature. The solvent was removed under reduced pressure to yield the crude amine salt which was used directly in the following reaction. m/z (ESI) 435.8 (M$^+$+H).

The amine salt was suspended in CH$_2$Cl$_2$ (2 mL), cooled to 0° C. and phosgene (15% in toluene, 0.24 mL, 0.36 mmol) was added followed by addition of triethylamine (0.14 mL, 1 mmol). After 1 hour, the reaction solution was concentrated under reduced pressure. The residue was dissolved in pyridine (3 mL), DiTBS-gemcitabine (0.147 g, 0.3 mmol) and DMAP (0.19 g, 1.5 mmol) was added. The reaction mixture was stirred at 70° C. overnight, concentrated under reduced pressure and the residue was purified by flash chromatography on silica gel. The obtained product was dissolved in THF (2 mL) and cooled to 0° C., TBAF (1M in THF solution, 1 mL, 1 mmol) was added. After 1 hour, the reaction mixture was concentrated under reduced pressure and the residue was purified by flash chromatography on silica gel to give compound 13. $^1$H NMR (CDCl$_3$) δ 12.8 (1H, br), 7.96 (1H, m), 7.64-7.56 (4H, m), 7.48-7.3 (4H, m), 7.24-6.98 (5H, m), 6.02 (1H, m), 5.09 (2H, m), 4.49 (1H, m), 4.1-3.85 (3H, m), 3.8-3.3 (4H, m), 3.2-2.8 (6H, m), m/z (ESI) 725.4 (M$^+$+H).

E.

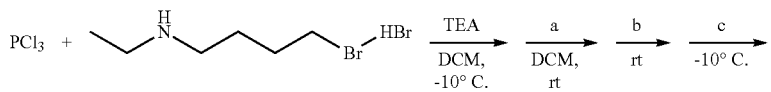

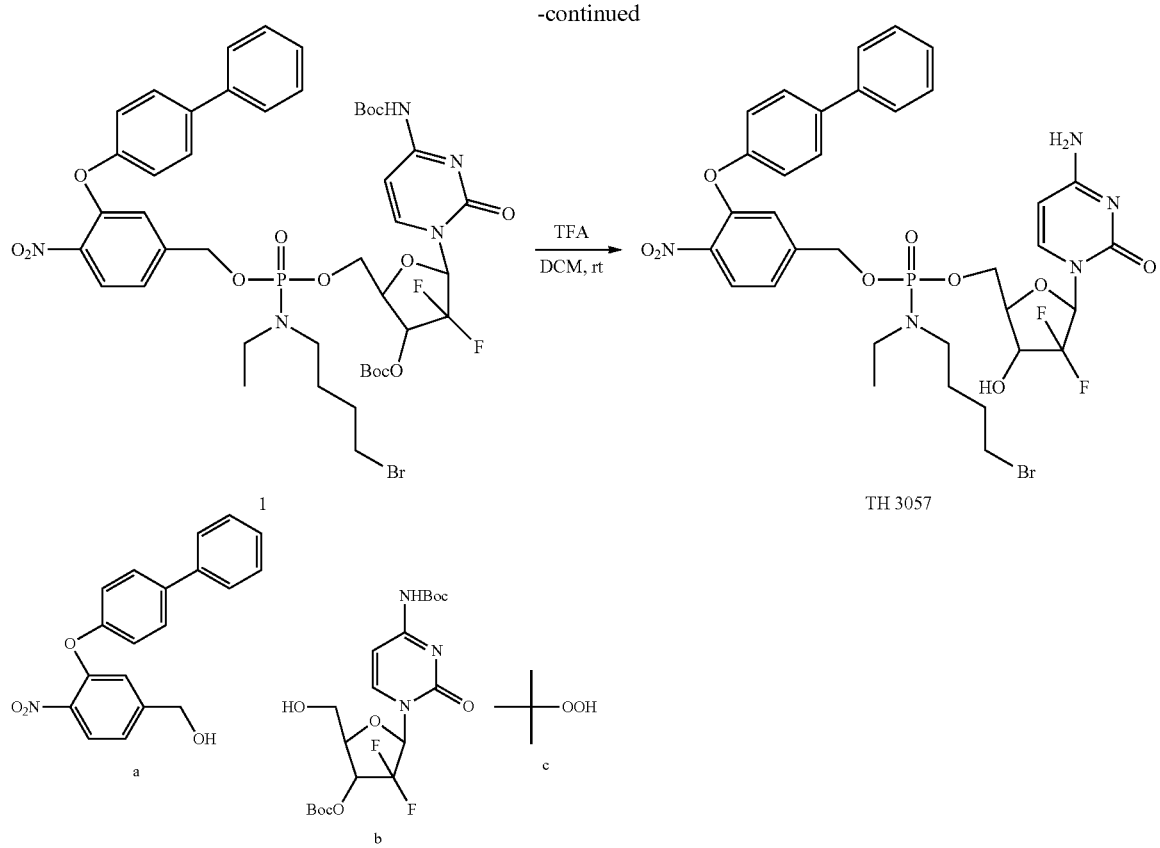

To a solution of (4-bromobutyl)(ethyl)amine hydrobromide (0.4 mmol, 104 mg) and PCl3 (0.4 mmol, 200 μl) in DCM (5 ml) was added TEA (2.4 mmol, 340 μl) slowly at −10° C. The resulting solution was stirred at room temperature for 10 min. A suspension of a (0.4 mmol, 130 mg) in DCM (2 ml) was added to the solution at room temperature, and the mixture was kept stirring for one hour. Solid b was added to reaction mixture and stirring another one hour at room temperature. Reaction was cooled to −10° C., and tert-butyl hydroperoxide (0.44 mmol, 88 μl, 5.5 M in decane) was added. After stirred at room temperature for 10 min, the reaction mixture was poured into cooled 5% HCl, extracted with DCM. Organic layer was washed with brine, dried with MgSO₄, filtered, concentrated. The residue was purified with flash chromatography (ethyl acetate in hexane, 0 to 100%) to give product 1. To a solution of product 1 in DCM (1 ml) was added TFA (I ml) at room temperature. The resulting solution was stirred for 30 min. Solvent was removed and the residue was dissolved in ethyl acetate. The ethyl acetate solution was washed with 10% NaHCO₃. The crude product was purified with flash chromatography (MeOH in DCM, 0 to 10%) to give product TH 3057 (15 mg). $^1$H NMR (d$_4$-MeOD, 400 MHz) δ 8.01-8.00 (dd, 1H), 7.75-7.7 (m, 3H), 7.61 (d, 2H), 7.43 (t, 2H), 7.36-7.29 (dd, 2H), 7.18-7.14 (m, 4), 6.2-6.1 (m, 1H), 6.0-5.9 (dd, 1H), 5.1-5.01 (m, 2H), 4.3-4.14 (m, 3H), 4.1-4.0 (m, 1H), 3.4-3.3 (m, 2H), 3.1-2.95 (m, 4H), 1.8-1.7 (m, 2H0, 1.7-1.55 (m, 2H), and 1.1-1.3 (t, 3H). $^{31}$P NMR (d$_4$-MeOD, 161.9 MHz) 11.93 (S) and 11.56 (S). $^{19}$F NMR (d$_4$-MeOD, 376.3 MHz) δ−77.35 (S).

Example 2

In Vitro Human Tumor Cell Line Cytotoxicity Assay

In vitro proliferation data on the H460 non cell lung cancer human tumor cell line is determined based on IC$_{50}$ measured by exposure of compounds at various concentrations for 2 hrs followed by a wash step and addition of fresh media followed by growth and cell viability staining and comparison to a media only treated control.

Specifically, exponentially growing cells are seeded at a density of 4×10³ cells per well in a 96 well plate and incubated at 37° C. in 5% CO₂, 95% air and 100% relative humidity for 24 hours prior to addition of test compounds. Compounds are solubilized in 100% DMSO at 200 times the desired final test concentration. At the time of drug addition, compounds are further diluted to 4 times the desired final concentration with complete medium. Aliquots of 50 μl of compound at specified concentrations are added to microtiter wells already containing 150 μl of medium, resulting in the final drug concentration reported. After drug addition the plates are incubated 72 hrs at 37° C., 5% CO2, 95% air and 100% relative humidity. At the end of this incubation, the viable cells are quantified using the AlamarBlue assay. The drug concentration resulting in growth inhibition of 50% (IC$_{50}$) is calculated using Prism software (Irvine, Calif.).

Cell proliferation were performed in the presence (3 micromolar) and absence of a specific inhibitor of the AKR 1C3 enzyme. The case of added inhibitor was added to cell culture 2 hours prior to compound treatment. The inhibitor used was compound 36 in Flanagan, et al, Bioorganic and Medicinal Chemistry (2014) p 962-977.

Proliferation data of TH compounds in H460 in the presence/absence of the specific AKR 1C3 inhibitor

| TH number | Structure | IC$_{50}$ (without inhibitor) (μM) | IC50 (with inhibitor) (μM) |
|---|---|---|---|
| TH3047 | 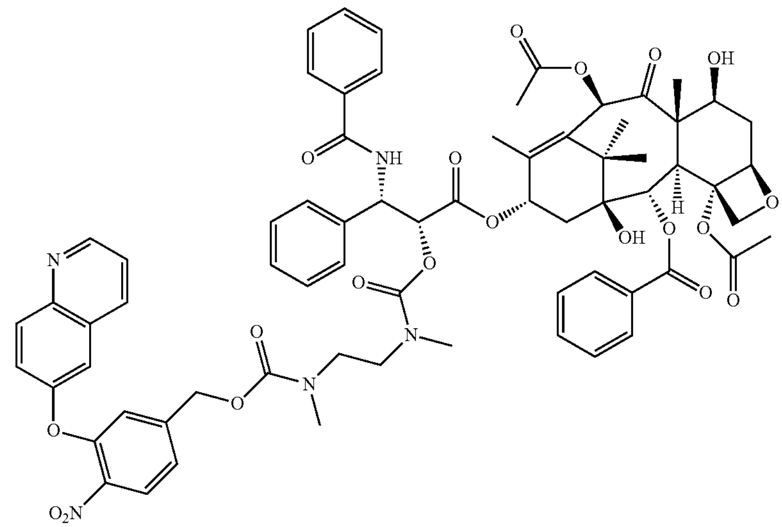 | 0.03 | 30 |
| TH3054 | 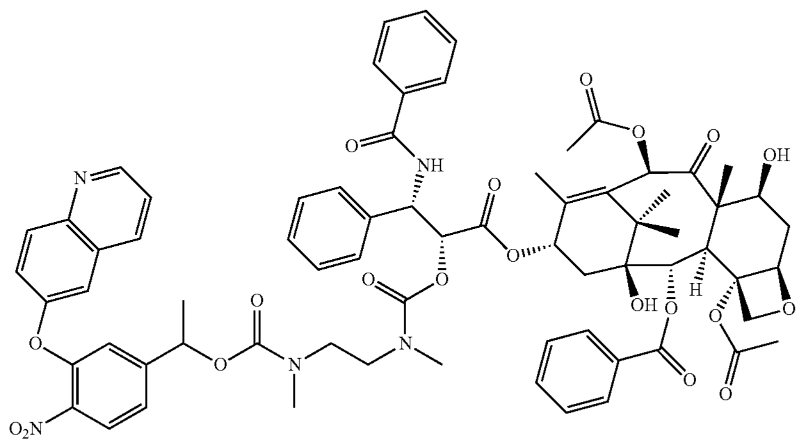 | 0.03 | 91 |
| TH3057 | 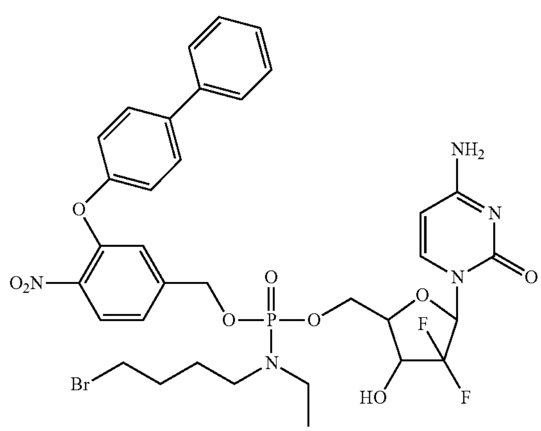 | 0.2 | 5 |

This data demonstrates the enhanced activation of the compounds above by human AKR 1C3

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. A compound of formula (I):

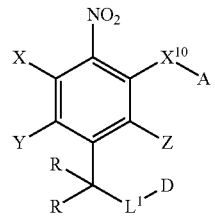

or a pharmaceutically acceptable salt, or a solvate thereof, wherein $X^{10}$ consists of O;

A is $C_6$-$C_{10}$ aryl, 5-15 membered heteroaryl, or —N=$CR^1R^2$;

each $R^1$ and $R^2$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each X, Y, and Z independently is hydrogen, CN, halo, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each R independently is hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each $R^{13}$ and $R^{14}$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, or ether;

wherein $L^1$ and D are defined as follows:

(1) $L^1$ is selected from the group consisting of:

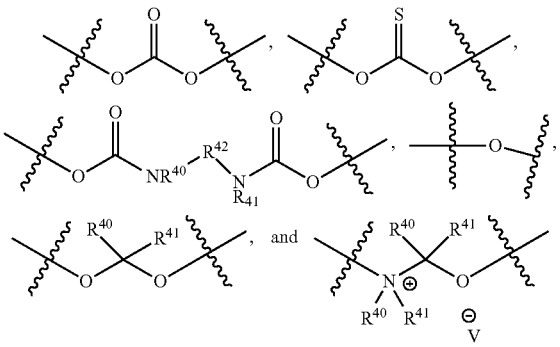

$R^{40}$ and $R^{41}$ are independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, or 5-15 membered heteroaryl;

$R^{42}$ is $C_2$-$C_3$ alkylene or heteroalkylene optionally substituted with 1-3 $C_1$-$C_6$ alkyl groups;

V(−) is any anion;

D is a moiety such that D-OH is an anti-cancer drug wherein OH is an aliphatic or a phenolic hydroxy group or is an OH moiety attached to a phosphorous atom; or (2) $L^1$ is:

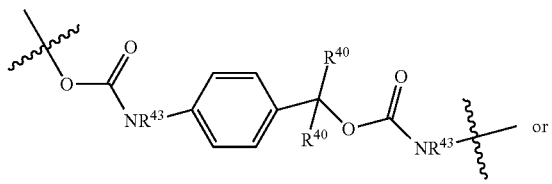

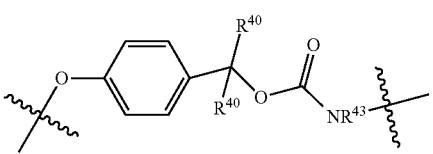

$R^{40}$ is defined as above, $R^{43}$ is hydrogen or together with D forms a heterocycle ring, and the phenylene moiety is optionally substituted, and D is a moiety such that D-$NR^{43}$H is an anti-cancer drug; or (3) $L^1$ is a bond, —O—$C(R^{40}R^{41})_2$—, —O—C$(R^{40}R^{41})$—$NR^{40}R^{41}$(+)-$C(R^{40}R^{41})$—, or

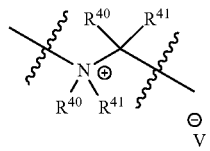

wherein $R^{40}$, $R^{41}$ and V are defined as above, and

D is an anticancer drug containing a tertiary or a secondary nitrogen atom, wherein the tertiary or the secondary nitrogen atom is bonded to $L^1$; and wherein the alkyl, alkenyl, alkynyl, cycloalkyl, aryl, heterocycle, heteroaryl, or ether groups are optionally substituted.

2. The compound of claim 1, wherein the compound is formula (1A-2) or (1A-3):

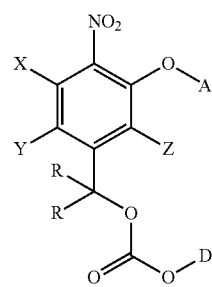

1A-2

-continued

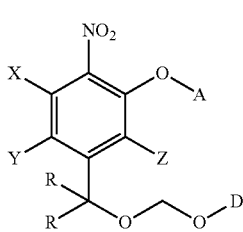

1A-3 wherein D is part of a cytotoxic agent, HO-D, containing at least one hydroxyl group, and the remaining variables are defined as in claim 1.

3. The compound of claim 1, wherein the compound is formula (1A-4), (1A-6), or (1A-6-i):

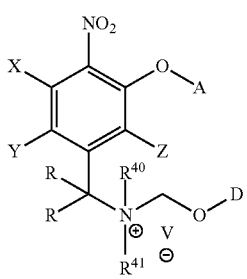

1A-4

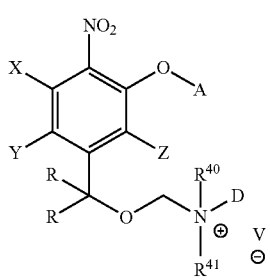

1A-6-i

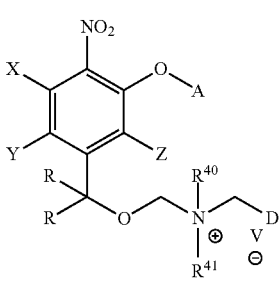

1A-6 wherein
in formula (1A-4), D is part of a cytotoxic agent, HO-D, containing at least one hydroxyl group,
in formula (1A-6-i), $DNR^{40}R^{41}$ is a drug,
in formula (1A-6), D is a drug containing a secondary nitrogen atom, where the secondary nitrogen atom is bonded to the methylene group as shown above, and the remaining variables are defined as in claim 1.

4. The compound of claim 1, wherein the compound is formula (1A-5) or (1A-7):

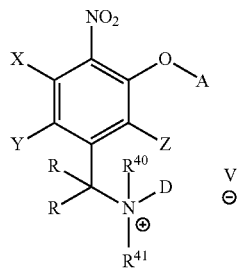

1A-5

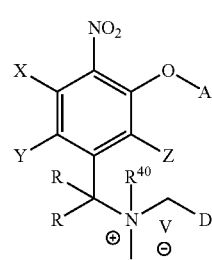

1A-7 wherein
in formula (1A-5), $DNR^{40}R^{41}$ is a drug,
in formula (1A-7), D is a drug containing a secondary nitrogen atom, where the secondary nitrogen atom is bonded to the methylene group as shown above, and the remaining variables are defined as in claim 1.

5. The compound of claim 1, wherein Z is hydrogen; X is hydrogen; and Y is hydrogen or halo.

6. The compound of claim 1, wherein A is $C_6$-$C_{10}$ aryl.

7. The compound of claim 6, wherein A is phenyl.

8. The compound of claim 1, wherein A is 5-15 membered heteroaryl.

9. The compound of claim 8, wherein A is pyridyl.

10. The compound of claim 1, wherein A is —N=$CR^1R^2$ where $R^1$ and $R^2$ are defined as in claim 1.

11. The compound of claim 1, wherein each R is hydrogen.

12. The compound of claim 1, wherein one of the R groups is hydrogen and the other R group is $C_1$-$C_6$ alkyl, or wherein both the R groups are non-hydrogen substituents as defined in claim 1.

13. The compound of claim 12, wherein R is methyl.

14. The compound of claim 1, wherein each of $R^{40}$, $R^{41}$, and $R^{43}$ is independently, hydrogen or methyl and $R^{42}$ is —$CH_2$—$CH_2$— or $CH_2$—$C(Me)_2$-.

15. A pharmaceutically acceptable composition comprising a compound of claim 1 and at least one pharmaceutically acceptable excipient or carrier.

16. The compound of claim 1, wherein the compound is
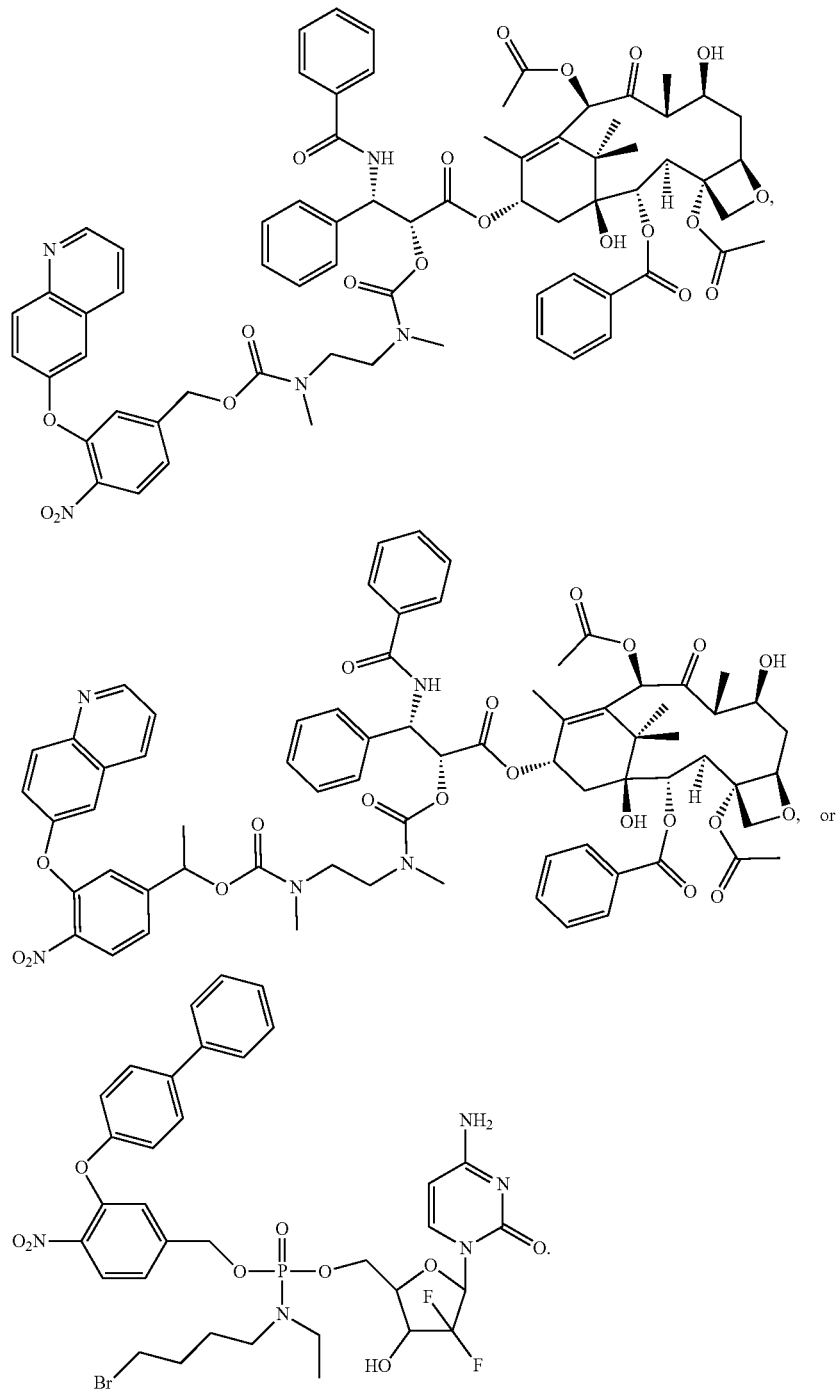
* * * * *